(12) United States Patent
Kilpatrick et al.

(10) Patent No.: US 7,326,238 B1
(45) Date of Patent: Feb. 5, 2008

(54) METHOD AND APPARATUS FOR TREATING VULNERABLE PLAQUE

(75) Inventors: Deborah Kilpatrick, Los Altos, CA (US); Murthy Simhambhatla, San Jose, CA (US); Santosh Prabhu, San Jose, CA (US); Shawn Chin Quee, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 285 days.

(21) Appl. No.: 10/262,149

(22) Filed: Sep. 30, 2002

(51) Int. Cl.
*A61F 2/06* (2006.01)
(52) U.S. Cl. .................. 623/1.13; 623/1.41; 623/1.42
(58) Field of Classification Search ............... 623/1.13, 623/1.41, 1.42
See application file for complete search history.

(56) References Cited

U.S. PATENT DOCUMENTS

| | | | |
|---|---|---|---|
| 4,512,338 A * | 4/1985 | Balko et al. ................ 606/108 |
| 6,100,443 A * | 8/2000 | Sims et al. .................... 800/14 |
| 6,117,166 A * | 9/2000 | Winston et al. ............. 623/1.13 |
| 6,419,659 B1 | 7/2002 | Phelps et al. |
| 6,451,044 B1 | 9/2002 | Naghavi et al. |
| 6,755,856 B2 * | 6/2004 | Fierens et al. ............. 623/1.15 |
| 6,905,476 B2 | 6/2005 | Ponzi |
| 2002/0062147 A1* | 5/2002 | Yang ........................ 623/1.13 |
| 2002/0193785 A1 | 12/2002 | Naghavi et al. |
| 2003/0060877 A1 | 3/2003 | Falotico et al. |
| 2003/0103995 A1 | 6/2003 | Hamblin |
| 2004/0220660 A1* | 11/2004 | Shanley et al. ............ 623/1.16 |
| 2004/0267354 A1* | 12/2004 | Ringeisen et al. ......... 623/1.42 |
| 2005/0004663 A1* | 1/2005 | Llanos et al. .............. 623/1.46 |

OTHER PUBLICATIONS

Mandrusov, Membrane-Based Cell Affinity Chromatography to Retrieve Viable Cells, Biotechnol, Prob. 1995, 11, 208-213, Artificial Organs Research Laboratory, Department of Chemical Engineering, Material Science and Metallurgy, Columbia University, New York, New York 10027, and Lousville, Lousville, Kentucky 40292.

Assmus, Transplantation of Progenitor Cells and Regeneration Enhancement in Acute Myocardial Infarction (TOPCARE-AMI), Clinical Investigation and Reports, Oct. 8, 2002, pp. 3009-3017, Department of Molecular Cardiology and Department of Hematology (H.M., D.H.) University of Frankfurt, Frankfurt, Germany, Circulation available at http://www.circulationha.org DOI: 10.1161/01.CIR.0000043246.74879CD.

* cited by examiner

*Primary Examiner*—Anhtuan T. Nguyen
*Assistant Examiner*—Elizabeth Houston
(74) *Attorney, Agent, or Firm*—Blakely, Sokoloff, Taylor & Zafman LLP

(57) ABSTRACT

An apparatus and method to treat vulnerable plaque. In one embodiment, the apparatus has a medical device to treat an occlusive plaque, and is also adapted to release a biologically active agent to treat vulnerable plaque located downstream from the occlusive plaque. In an alternative embodiment, the apparatus has an expandable tube attached to the inner surface of a stent, and a layer of endothelial cells seeded on the inner surface of the expandable tube. The expandable tube shields a vulnerable plaque from a body lumen.

8 Claims, 22 Drawing Sheets

FIBROATHEROMA TYPE VULNERABLE PLAQUE

VULNERABLE PLAQUE TREATMENT

METHOD AND APPARATUS FOR TREATING VULNERABLE PLAQUE

FIELD OF THE INVENTION

The invention, in one embodiment, relates generally to the treatment of coronary disease, and more particularly, in one embodiment, to the stabilization of vulnerable plaque.

BACKGROUND OF THE INVENTION

Coronary heart disease is generally thought to be caused by the narrowing of coronary arteries by atherosclerosis, the buildup of fatty deposits in the lining of the arteries. The process that may lead to atherosclerosis begins with the accumulation of excess fats and cholesterol in the blood. These substances infiltrate the lining of arteries, gradually increasing in size to form deposits commonly referred to as plaque or atherosclerotic occlusions. Plaques narrow the arterial lumen and impede blood flow. Blood cells may collect around the plaque, eventually creating a blood clot that may block the artery completely.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen which produces symptoms. As such, conventional methods for detecting heart disease, such as an angiogram, may not detect vulnerable plaque growth into the arterial wall. After death, an autopsy can reveal the plaque congested in arterial wall that could not have been seen otherwise with currently available medical technology.

The intrinsic histological features that may characterize a vulnerable plaque include increased lipid content, increased macrophage, foam cell and T lymphocyte content, and reduced collagen and smooth muscle cell (SMC) content. This fibroatheroma type of vulnerable plaque is often referred to as "soft," having a large lipid pool of lipoproteins surrounded by a fibrous cap. The fibrous cap contains mostly collagen, whose reduced concentration combined with macrophage derived enzyme degradations can cause the fibrous cap of these lesions to rupture under unpredictable circumstances. When ruptured, the lipid core contents, thought to include tissue factor, contact the arterial bloodstream, causing a blood clot to form that can completely block the artery resulting in an acute coronary syndrome (ACS) event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, in addition to in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

FIG. 1A illustrates a partial cross-section of an artery having a narrowed arterial lumen caused by the presence of occlusive atherosclerosis. Plaque accumulates to impede and reduce blood flow through the arterial lumen and thus often causes symptoms (e.g., angina pectoris). The arrows indicate the direction of blood flow through the arterial lumen. FIG. 1B illustrates an occlusive atherosclerosis within an arterial lumen resulting in significant reduction in lumen patency. This type of atherosclerosis can easily be detected through current diagnostic methods such as an angiogram. FIG. 1B also illustrates, downstream from the occlusive atherosclerosis, a fibroatheroma type of vulnerable plaque. The vulnerable plaque, with a lipid core, develops mostly within the arterial wall with minimal occlusive effects such that it is not easily detected by current diagnostic methods. This is partially due to a phenomenon known as "positive remodeling," which allows the vessel to respond to the presence of disease. The fibroatheroma vulnerable plaque has grown into the positively remodeled arterial wall so that vessel occlusion has not been manifested. A fibrous cap surrounds the vulnerable plaque.

FIGS. 2A-2C illustrate a cross-sectional view of the accumulation of vulnerable plaque in the arterial wall. FIG. 2A illustrates an arterial wall that is not affected by atherosclerosis. The normal arterial wall consists of an intima layer, a media layer, and an adventitia layer. The intima is in direct contact with the blood flow within the arterial lumen. The intima consists mainly of a monolayer of endothelial cells. The media consists mostly of smooth muscle cells and extracellular matrix proteins. The outermost layer of the arterial wall, the adventitia, is primarily collagenous and contains nerves, blood vessels, and lymph vessels. FIG. 2B illustrates the large presence of a fibroatheroma type vulnerable plaque surrounded by a fibrous cap within the arterial wall. The vulnerable plaque consists mainly of a large lipid core. The fibrous cap layer shields the lumen of the artery from the thrombogenic components in the core. FIG. 2C illustrates an occlusive thrombosis event resulting from the rupturing of the fibrous cap. Thrombogenic components in the vulnerable plaque contact luminal blood and cause the thrombotic event.

Autopsy studies and other evidence strongly suggest that the presence of a current acute coronary syndrome (ACS) event and/or existing thrombus at certain plaque sites may correlate to predicting a future ACS event in a given patient. The latter indicates the likelihood of a prior thrombotic event (e.g., fibroatheroma rupture) after which the plaque was able to heal itself, or complete occlusion of the vessel was somehow prevented. Autopsy studies also indicate that it is reasonable to expect that at least one vulnerable plaque could exist in the majority of catheterization laboratory patients being treated for arterial blockage from visible, occlusive atherosclerosis. Many of the patients at highest risk, therefore, for future ACS events may already be receiving interventional treatment, even though current methods to diagnose occlusive plaques (i.e., non-vulnerable type plaque) are not effective for enabling therapy for vulnerable plaque. Furthermore, treating both the occlusive plaques and the vulnerable plaque in one procedure might be beneficial and desirable compared to separate treatments. This would provide a greater convenience to the patient and for the physician.

SUMMARY OF THE INVENTION

An apparatus and method to treat vulnerable plaque are described. In one embodiment, the apparatus includes a medical device to treat an occlusive plaque, and is also adapted to release a biologic or biologically active agent to treat (e.g., stabilize) vulnerable plaque located downstream from the occlusive plaque.

BRIEF DESCRIPTION OF THE DRAWINGS

The present invention is illustrated by way of example, and not limitation, in the figures of the accompanying drawings in which.

DETAILED DESCRIPTION

In the following description, numerous specific details are set forth such as examples of specific, components, processes, etc. in order to provide a thorough understanding of various embodiment of the present invention. It will be apparent, however, to one skilled in the art that these specific details need not be employed to practice various embodiments of the present invention. In other instances, well known components or methods have not been described in detail in order to avoid unnecessarily obscuring various embodiments of the present invention. The term "coupled" as used herein means connected directly to or indirectly connected through one or more intervening components, structures or elements. The terms "drugs," "bioactive agents," and "therapeutic agents" are used interchangeably to refer to agents (e.g., chemical substances) to treat, in one embodiment, coronary artery and related diseases including for example, atherosclerotic occlusions and vulnerable plaque.

Apparatuses and their methods of use to treat vulnerable plaque are described. In one embodiment, the vulnerable plaque or the region of the artery containing the vulnerable plaque may be treated alone or in combination with treating occlusive atherosclerosis. The benefit is that any vulnerable, but not yet occlusive plaques would be treated without having to place a therapeutic implant (e.g., a stent) at the vulnerable plaque region. The only implant placed would be that already being used to scaffold and treat the existing occlusive plaque. In the following description, the stabilization of vulnerable plaque is described with respect to treatment within the artery. The coronary artery is just one region in the body where vulnerable plaque may form. As such, it can be appreciated that the stabilization of vulnerable plaque may be achieved in any vessel of the body where vulnerable plaque may exist.

Figure 1A:
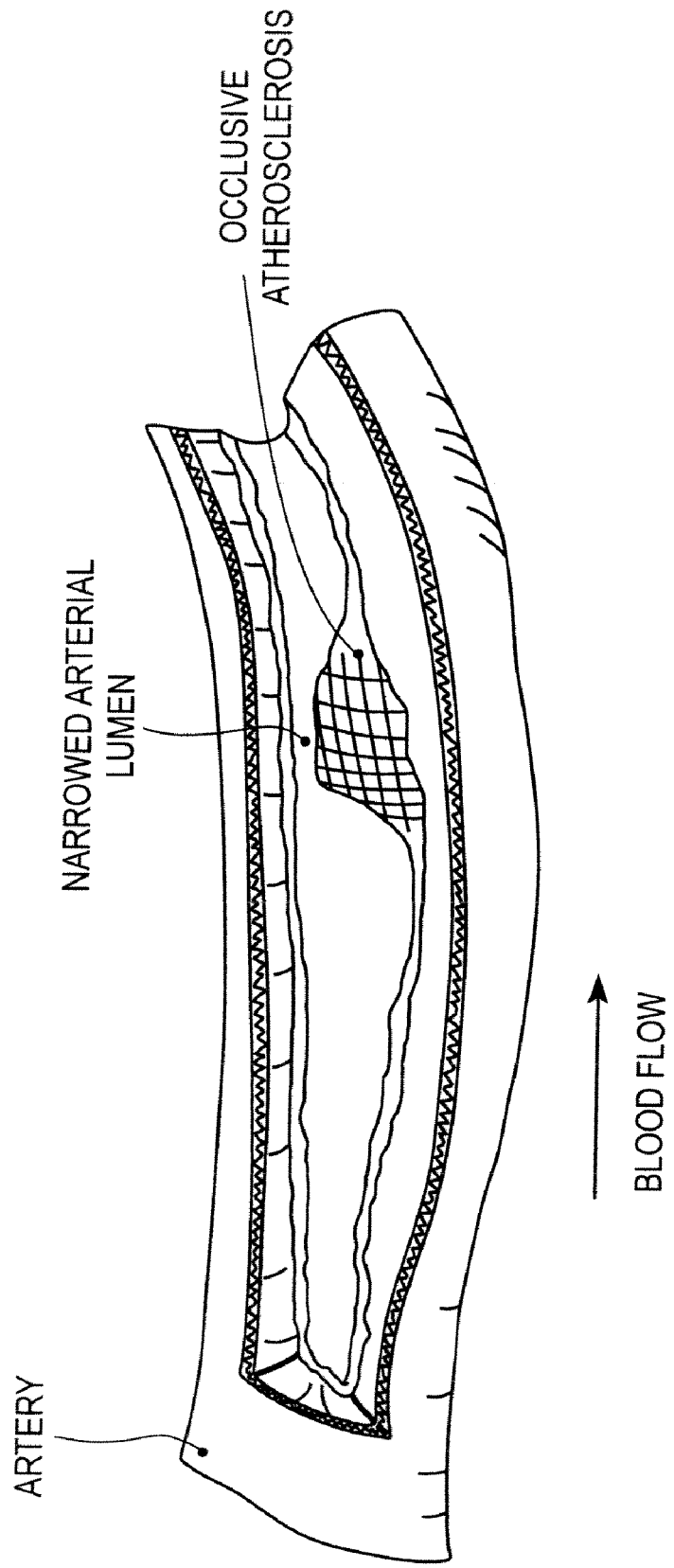
FIG. 1A illustrates a partial cross-section of an arterial lumen having occlusive plaque.
Figure 1B:
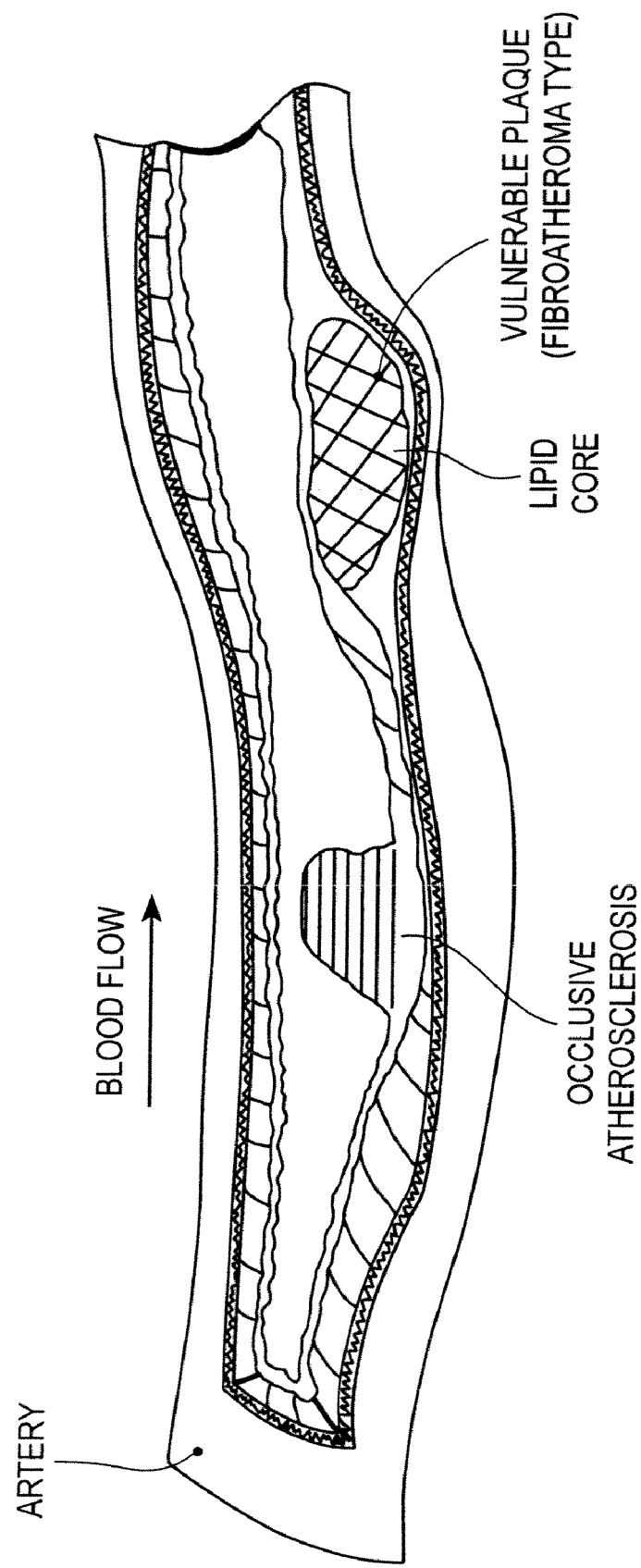
FIG. 1B illustrates a partial cross-section of an arterial lumen having occlusive plaque and vulnerable plaque.
Figure 2A:
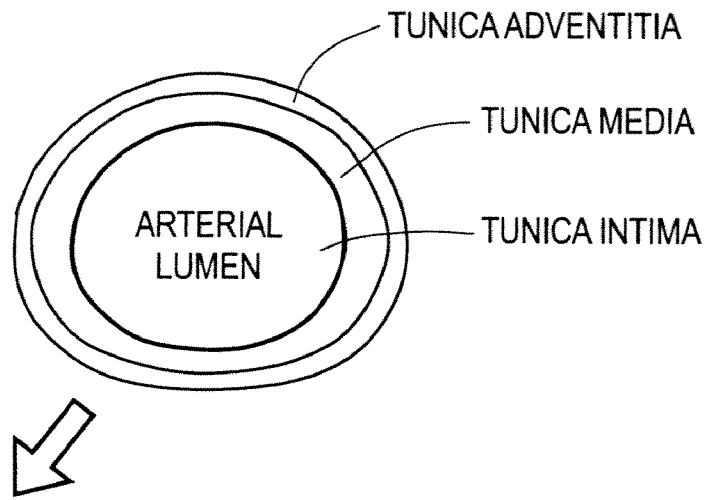
FIGS. 2A-2C illustrate the vessel morphology and the rupturing of a vulnerable plaque.
Figure 2B:
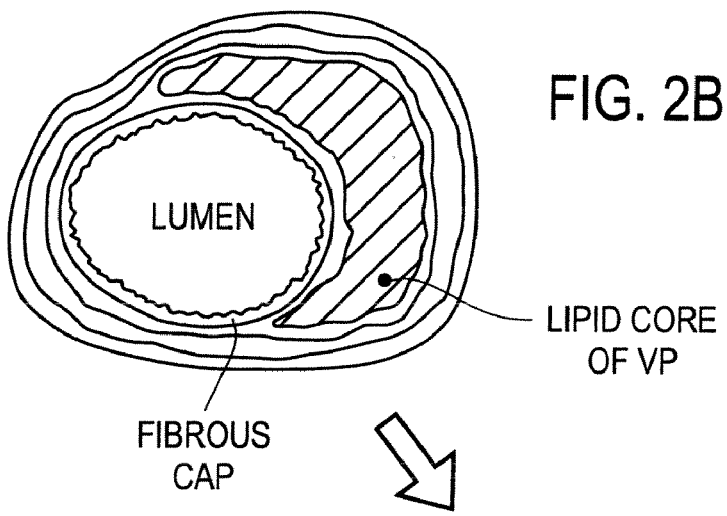
Figure 2C:
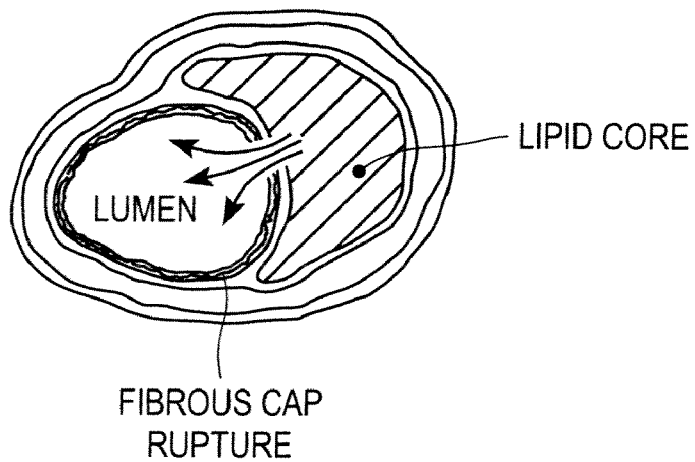
Figure 3A:
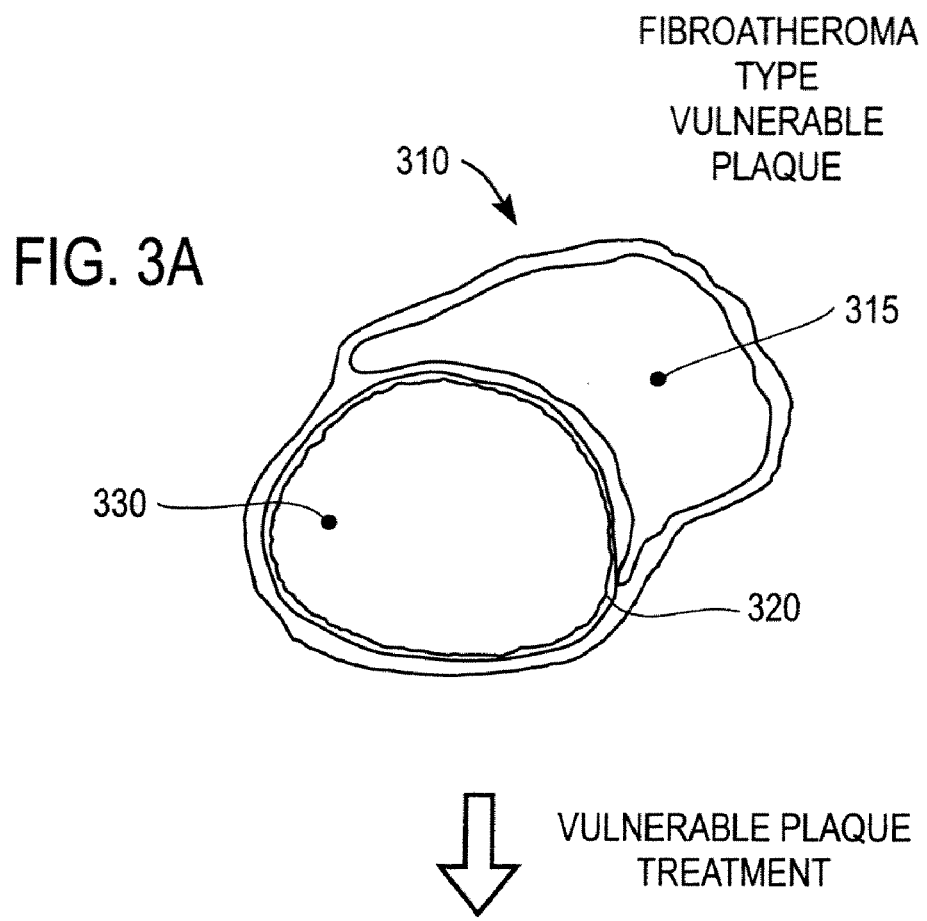
FIGS. 3A-3B illustrate the stabilization a vulnerable plaque by reducing the size of the lipid core and strengthening and increasing the thickness of the fibrous cap.
Figure 3B:
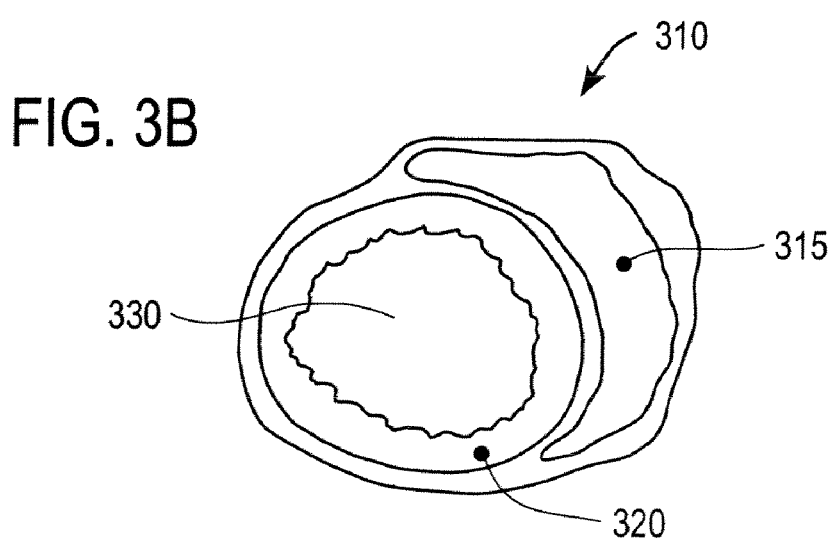

FIGS. 3A-3B illustrate a cross-sectional view of the stabilization of vulnerable plaque. FIG. 3A shows a large vulnerable plaque 310 having lipid core 315 separated from arterial lumen 330 by thin fibrous cap 320. Thin fibrous caps and reduced collagen content or degraded collagen in the fibrous caps increase a plaque's vulnerability to rupture. As illustrated in FIG. 3B, vulnerable plaque 310 has been stabilized by thickening and/or strengthening fibrous cap 320 that separates lipid core 315 from arterial lumen 330. This reduces the likelihood of fibrous cap 320 rupturing. Additionally, lipid core 315 redistribution has occurred in combination with strengthening fibrous cap 320. Vulnerable plaque 310 may also be treated by inducing collateral artery or vessel growth near the vulnerable plaque region such that, in the event of fibrous cap rupture or occlusive thrombosis, an alternative blood path exists to bypass the ruptured region (not shown).

Drug Eluting Stents

In one embodiment, a drug eluting stent may be implanted at the region of vessel occlusion that may be upstream from a vulnerable plaque region. As discussed above, autopsy studies have shown that vulnerable plaque regions commonly exist in the vicinity of occlusive plaques. A medical device, such as a drug eluting stent, may be used to treat the occlusive atherosclerosis (i.e., non-vulnerable plaque) while releasing a drug or biologically active agent to treat a vulnerable plaque region distal or downstream to the occlusive plaque. The drug may be released slowly over time, and may include for example, anti-inflammatory or anti-oxidizing agents. Biologically active agents may also be released include cells, proteins, peptides, and related entities.

The eluting stent may have the vulnerable plaque treating drug or agent dispersed on the surface of the stent, or co-dissolved in a matrix solution to be dispersed on the stent. Other methods to coat the stent with a vulnerable plaque treating drug include dip coating, spin coating, spray coating, or other coating methods commonly practiced in the art.

In one embodiment, therapeutic or biologically active agents may be released to induce therapeutic angiogenesis, which refers to the processes of causing or inducing angiogenesis and arteriogenesis, either downstream, or away from the vulnerable plaque. Arteriogenesis is the enlargement of pre-existing collateral vessels. Collateral vessels allow blood to flow from a well-perfused region of the vessel into an ischemic region (from above an occlusion to downstream from the occlusion). Angiogenesis is the promotion or causation of the formation of new blood vessels downstream from the ischemic region. Having more blood vessels (e.g., capillaries) below the occlusion may provide for less pressure drop to perfuse areas with severe narrowing caused by a thrombus. In the event that an occlusive thrombus occurs in a vulnerable plaque, the myocardium perfused by the affected artery is salvaged. Representative therapeutic or biologically active agents include, but are not limited to, proteins such as vascular endothelial growth factor (VEGF) in any of its multiple isoforms, fibroblast growth factors, monocyte chemoatractant protein 1 (MCP-1), transforming growth factor alpha (TGF-alpha), transforming growth factor beta (TGF-beta) in any of its multiple isoforms, DEL-1, insulin like growth factors (IGF), placental growth factor (PLGF), hepatocyte growth factor (HGF), prostaglandin E1 (PG-E1), prostaglandin E2 (PG-E2), tumor necrosis factor alpha (TBF-alpha), granulocyte stimulating growth factor (G-CSF), granulocyte macrophage colony-stimulating growth factor (GM-CSF), angiogenin, follistatin, and proliferin, genes encoding these proteins, cells transfected with these genes, pro-angiogenic peptides such as PR39 and PR11, and pro-angiogenic small molecules such as nicotine.

In another embodiment, therapeutic or biologically active agents to treat the vulnerable plaque may be delivered through the bloodstream or vessel wall. These therapeutic or biologically active agents include, but are not limited to, lipid lowering agents, antioxidants, extracellular matrix synthesis promoters, inhibitors of plaque inflammation and extracellular degradation, estradiol drug classes and its derivatives.

Prospective studies of high-risk patients in whom complex plaques were found have indicated that many of the ACS events can happen within six months to one year after a patient has an occlusive atherosclerosis lesion treated. In other words, there is a clinical reason to believe that it would be efficacious to try and actively treat lesions in those patients for a three to six-month period of time after treatment of occlusive atherosclerosis to prevent a recurrent ACS event. Examples of devices to treat vulnerable plaque regions include drug eluting stents, and drug loaded bioerodable and bioadhesive microparticles.

In one embodiment, the polymer may be coated on a stent using dip coating, spin coating, spray coating or other coating methods known in the art. The drug can alternatively be encapsulated in microparticles or nanoparticles and dispersed in a stent coating. A diffusion limiting top-coat may optionally be applied to the above coatings. The active agents may optionally be loaded on a stent together either by adding them together to the solution of the matrix polymer before coating, or by coating different layers, each containing a different agent or combination of agents. The drug eluting stent can alternatively have an active agent or a combination of agents dispersed in a bioerodable stent forming polymer.

Vulnerable plaque regions may also be treated independent of treating occlusive lesions near the vulnerable plaque regions. In another embodiment, a vulnerable plaque treatment drug or biologically active agent may be injected through or around the fibrous cap of a vulnerable plaque. Alternatively, in the event of a thrombotic event, a drug may be injected to prevent complete occlusion of the vessel. In one embodiment, a needle catheter may be used to inject the drug. The needle catheter may be modified to accommodate the following targets around the vulnerable plaque: fibrous cap, proteoglycan-rich surface layer, subintimal lipid core, proximal or distal regions of the plaque, media containing smooth muscle cells around the lipid core, and peri-adventitial space. In another embodiment, the needle catheter may include a sensing capability to determine penetration depth of the needle. Furthermore, the needle catheter may be configured to adopt balloons of various sizes to control the angle of needle penetration. Moreover, the use of balloons would enable accurate penetration of the needle at the desired target.

In another embodiment, a drug eluting stent may be used to strengthen or increase the thickness of the fibrous cap of the vulnerable plaque in a controlled manner. Increasing the thickness of the fibrous cap may redistribute and lower the stresses in the fibrous cap. This may stabilize the plaque and prevent it from rupturing.

Figure 4:
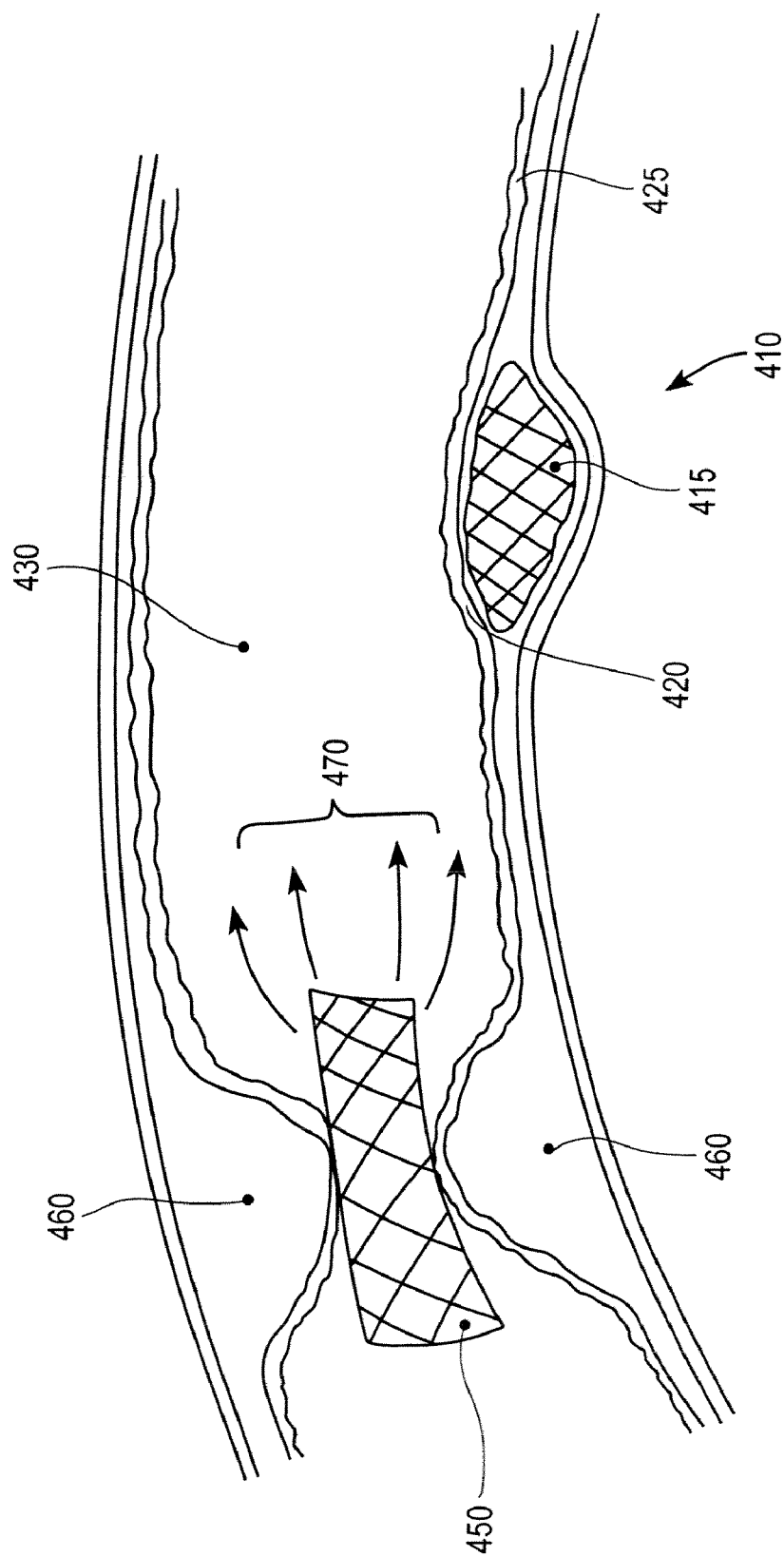
FIG. 4 illustrates one embodiment of using a drug delivery stent to treat a vulnerable plaque downstream from an occlusive plaque.

Referring to FIG. 4, a drug delivery stent 450 to treat a vulnerable plaque region is illustrated. Stent 450 is disposed in an arterial lumen 430 to treat both occlusive plaque 460 and vulnerable plaque 410 located downstream from occlusive plaque 460. As illustrated, stent 450 releases a drug (indicated by arrows 470) to treat the vulnerable plaque 410. As discussed above, vulnerable plaque regions commonly exist near occlusive plaque, and treating both might be advantageous over separate procedures. Occlusive plaque 460 has grown to cause a narrowing of the arterial lumen 430. Stent 450 is shown in a state before expansion to enlarge the diameter of the arterial lumen 430. A dilation balloon (not shown) may be used to expand stent 450, or stent 450 may be made of a material that self-expands (e.g., Nitinol) so that a dilation balloon is not needed.

As illustrated in FIG. 4, vulnerable plaque 410 is located downstream of the occlusive plaque 460 but does not show any vessel occlusion. Vulnerable plaque 410 has soft lipid core 415 with fibrous cap 420 separating vulnerable plaque 410 from arterial lumen 430. As indicated by arrows 470, stent 450 releases a drug or biologically active agent through the bloodstream of arterial lumen 430 to treat vulnerable plaque 410. In one embodiment, lipid lowering agents may be released. Lowering of serum LDL cholesterol may lead to a reduction in the amount of cholesterol entering vulnerable plaque 410, and increases high density lipoprotein (HDL) cholesterol which may contribute to active LDL removal from the vessel wall 425. Animal studies have shown that removal of lipid increases the relative collagen content of fibrous cap 420 and could increase the production of collagen, favoring vulnerable plaque stabilization. Lipid lowering animal studies suggest this also treats vulnerable plaque 410 by reducing local inflammation and the expression and activity of matrix-degrading enzymes, favoring collagen accumulation in fibrous cap 420, making it more resistant to rupture. Lipid lowering agents may also change the composition of lipid core 415 to promote plaque stabilization. It is thought that the lipid lowering agents may convert the high concentration of cholesterol esters to insoluble cholesterol monohydrate crystals, resulting in a more stiff lipid core 415 that is more resistant to plaque rupture. Lipid lowering agents include, but are not limited to hydroxy-methylglutaryl coenzyme A (HMG CoA) reductase inhibitors, niacin, bile acid resins, and fibrates.

Examples of doses of agents which may be used with embodiments of the invention, such as a drug delivery stent (i.e., the stent having been loaded with a drug which is eluted/released over time or a needle catheter) are described herein. The particular effective dose may be modified based on therapeutic results, and the following exemplary doses are acceptable initial levels which may be modified based on therapeutic results.

In an alternative embodiment, antioxidants may be released from stent 450. The oxidation of LDL cholesterol appears to have negative impact upon vessel processes during atherogenesis. Oxidized LDL binds to cell receptors on macrophages and contributes to foam cell formation. As such, antioxidants, through their inhibition of LDL oxidation, may contribute to plaque stabilization. Antioxidants may also promote plaque stabilization by reducing matrix degradation within vulnerable plaque 410. Examples of antioxidants include, but are not limited to vitamin E (α-tocopherol), vitamin C, and β-carotene supplements. Additionally, HMG CoA reductase inhibitors may also reduce oxidized LDL levels by increasing the total antioxidant capacity of plasma.

Lipid lowering agents such as statins and antioxidants may be administered at a level of about 0.5 mg/kg per day; higher doses (e.g., 5 times higher) appear to inhibit angiogenesis. See Weis et al., *Statins Have Biphasic Effects on Angiogenesis*, Circulation, 105(6):739-745 (Feb. 12, 2000). This dosage level may be achieved by loading a stent with about 10-600 μg of the statin, where the stent is designed to elute the statin over a period of 8 weeks. In one embodiment, the stent may have a length of 13 mm and a diameter of 3 mm.

In one embodiment, the stent may have a drug release rate of 150 μg over 10 hours, or 15 μg per hour. In another embodiment, the stent may have a lower release rate of about 20 μg over 10 hours, over 2 μg per hour. Additionally, a compound called "AGI-1067", developed by AtheroGenics, Inc. of Alpharetta, Ga., may be loaded onto the stent. AGI-1067 has been shown in studies to have direct anti-atherosclerotic effect on coronary blood vessels, consistent with reversing the progression of coronary artery disease.

In an alternative embodiment, extracellular matrix synthesis promoters may be released from stent 450. Reduced collagen content in fibrous cap 420 may result from decreased synthesis of extracellular matrix by smooth muscle cells (SMC) and/or increased breakdown by matrix-degrading proteases, thereby leading to thinning and weakening of fibrous cap 420, predisposing vulnerable plaque 410 to rupture with hemodynamic or mechanical stresses.

Vascular SMC synthesize both collagenous and noncollagenous portions of the extracellular matrix. Lack of sufficient SMC to secrete and organize the matrix in response to mechanical stress could render fibrous cap 420 more vulnerable to weakening by extracellular matrix degradation. Atherosclerosis and arterial injury lead to increased synthesis of many matrix components. In contrast, vulnerable plaque, in general, lacks a sufficient quantity of healthy matrix to provide strength to the fibrous cap to prevent rupture. Thus, promotion of SMC proliferation may lead to plaque stabilization. Delivery of cytokines and growth factors may also achieve SMC proliferation. SMC promoters and proliferative agents such as lysophosphatidic acid may be loaded onto a stent for delivery within a vessel. See Adolfsson et al., *Lysophosphatidic Acid Stimulates Proliferation of Cultured Smooth Muscle Cells from Human BPH Tissue: Sildenafil and Papaverin Generate Inhibition*, Prostate, 51(1):50-8 (Apr. 1, 2002). For example, a SMC promoter may be administered at a level of about 0.5 mg/kg per day to higher doses of about 2.5 mg/kg per day. This dosage level may be achieved by loading a stent with about 10-600 μg of the SMC promoter, where the stent is designed to elute the drug over a period of 8 weeks. In one embodiment, the stent may have a drug release rate of 150 μg over 10 hours, or 15 μg per hour. In another embodiment, the stent may have a lower release rate of about 20 μg over 10 hours, over 2 μg per hour.

In an alternative embodiment, inhibitors of plaque inflammation and extracellular matrix degradation may be released from stent 450. Increased matrix degrading activity associated with enzymes derived from cells such as vascular SMC, macrophages and T lymphocytes is a common finding in vulnerable plaque. Studies suggest that matrix metalloproteinases (MMPs) are involved in matrix degradation. Plaque stabilization could be achieved through inhibition of extracellular matrix degradation by preventing the accumulation of macrophages and T lymphocytes in the vulnerable plaque or by inhibiting the proteolytic enzyme cascade directly. Possible methods to achieve MMP inhibition include increasing the levels of natural inhibitors (TIMPs) either by exogenous administration of recombinant TIMPs or administrating synthetic inhibitors. Synthetic inhibitors of MMPs, including tetracycline-derived antibiotics, anthracyclines and synthetic peptides may also be used. MMP inhibitors may be themselves antioxidants and statins based on preclinical animal data. Studies have shown MMP inhibitors, such as cerivastatin to significantly reduce tissue levels of both total and active MMP-9 in a concentration-dependent manner. See Nagashima et al., *A 3-hydroxy-3-methylglutaryl Coenzyme A Reductase Inhibitor, Cerivastatin, Supresses Production of Matrix Metalloproteinase-9 in Human Abdominal Aortic Aneurysm Wall*, J. Vascular Surgery, 36(1);158-63 (July 2002). As with statins as described above, MMP inhibitors may be administered at a level of about 0.5 mg/kg per day to higher doses of about 2.5 mg/kg per day. This dosage level may be achieved by loading a stent with about 10-600 μg of the SMC promoter, where the stent is designed to elute the drug over a period of 8 weeks. In one embodiment, the stent may have a drug release rate of 150 μg over 10 hours, or 15 μg per hour. In another embodiment, the stent may have a lower release rate of about 20 μg over 10 hours, over 2 μg per hour. Additionally, Avasimibe, an ACAT (Acyl-CoA: cholesterol acyltransferase) inhibitor, in the 10 mg/kg range appears to impact MMPs and plaque burden, as well as monocyte adhesion. See Rodriguez and Usher, *Anti-atherogenic Effects of the acyl-CoA: Cholesterol Acyltransferase Inhibitor, Avasimibe (Cl-1011), in Cultured Primary Human Macrophages*, Atherosclerosis, 161(1); 45-54 (March 2002).

Dosages and concentrations described above are exemplary, and other dosages may be applied such that when delivered over a biologically relevant time at the appropriate release rate, gives a biologically relevant concentration. The biologically relevant time may depend on the biologic target but may range from several hours to several weeks with the most important times being from 1 day to 42 days. Dosages may also be determined by conducting preliminary animal studies and generating a dose response curve. Maximum concentration in the dose response curve could be determined by the solubility of a particular compound or agent in the solution and similarly for coating a stent.

Figure 12:
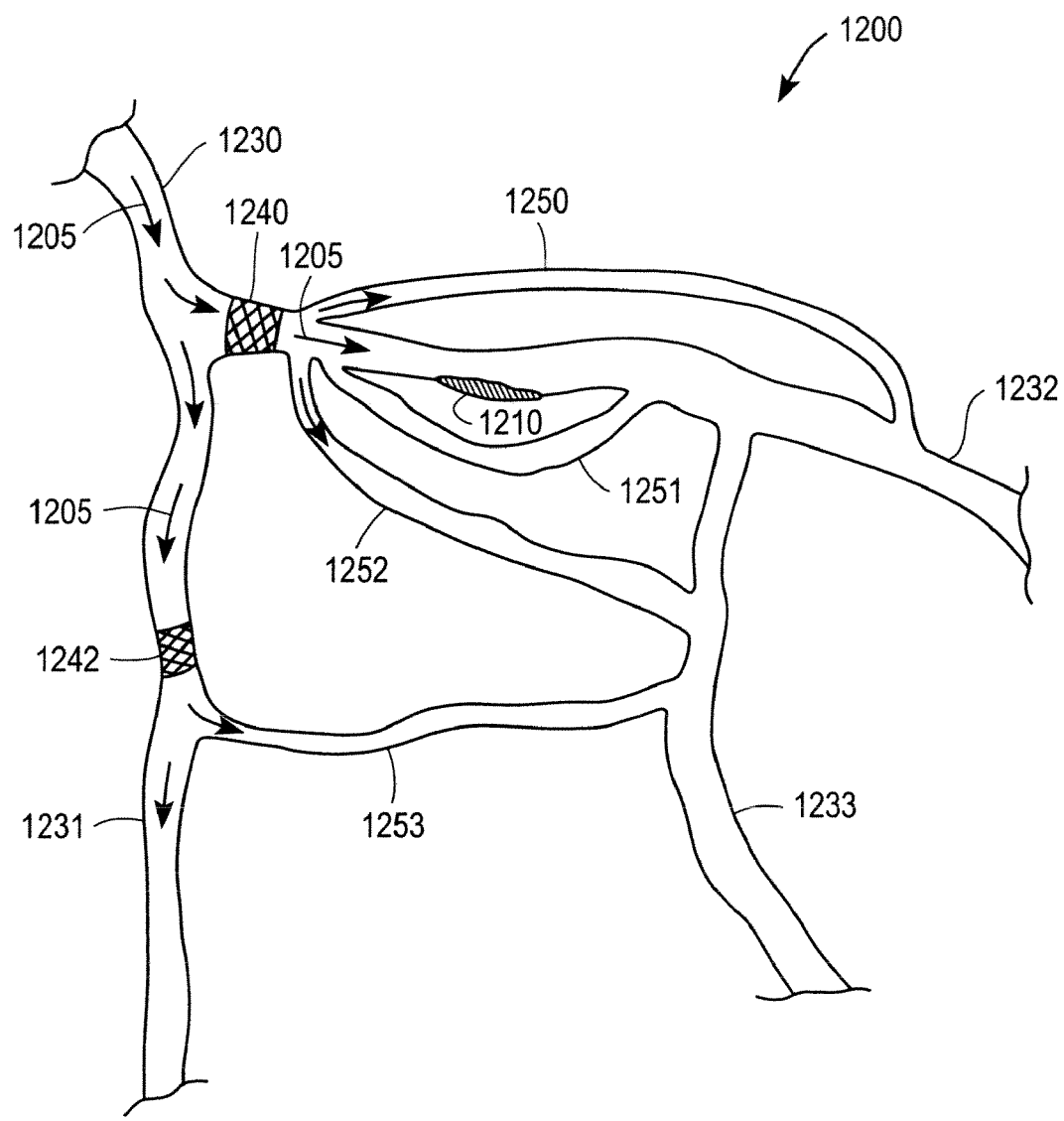
FIG. 12 illustrates one embodiment of inducing collateral vessel growth near a vulnerable plaque.

In yet another alternative embodiment, the active agent may induce collateral artery or vessel growth (i.e., angiogenesis or arteriogenesis) near the vulnerable plaque region such that, in the event of a plaque rupture and subsequent occlusive thrombosis, secondary blood paths may bypass the ruptured region and allow for continued blood flow throughout the artery. FIG. 12 illustrates one embodiment of arterial section 1200 with collateral vessels that have been induced with an active agent. Collateral vessels 1250, 1251, 1252 and 1253 provide paths for blood flow to continue through arterial section 1200 either temporarily until the occlusion is treated, or permanently to provide greater blood flow. The active agent has been delivered through drug delivery stents 1240 and 1242. Primary artery 1230 branches into sections 1231, 1232, and 1233 and arrows 1205 indicate the direction of blood flow through arterial section 1200. Vulnerable plaque 1210 is disposed within arterial branch 1232. Stent 1240 induces the growth of collateral vessels 1250, 1251 and 1252 around vulnerable plaque 1210. Collateral vessel 1251 starts upstream(near stent 1240) from vulnerable plaque 1210 and ends just downstream from vulnerable plaque 1210. Collateral vessel 1250 starts upstream from vulnerable plaque 1210 and ends further downstream of arterial branch 1232. Collateral vessel 1252 starts upstream from vulnerable plaque 1210 and ends at arterial branch 1233.

Alternatively, collateral vessel growth may be induced from an arterial branch that does not contain a vulnerable plaque. Stent 1242 carrying an active agent is disposed within arterial branch 1231 which induces collateral vessel 1253 from arterial branch 1231 to branch 1233. As such, collateral vessel 1253 may provide an alternate pathway for continued blood flow in the event vulnerable plaque 1210 ruptures. Although therapeutic or biologically active agents for angiogenesis and arteriogenesis have been described above with respect to drug eluting stents, other types of medical devices may be utilized. In one embodiment, for example, needle catheters may be used to deliver agents to induce angiogenesis and/or arteriogenesis. Needle catheters are described in greater detail below with respect to FIGS. 9-10.

In one embodiment, therapeutic or biologically active agents may be released to induce arteriogenesis or angiogenesis either downstream, or away from the vulnerable plaque to the myocardium. In the event that an occlusive thrombus occurs from a vulnerable plaque, the myocardium perfused by the affected artery may be salvaged. Representative therapeutic or biologically active agents include, but are not limited to, proteins such as vascular endothelial growth factor (VEGF) in any of its multiple isoforms, fibroblast growth factors, monocyte chemoatractant protein 1 (MCP-1), transforming growth factor alpha (TGF-alpha), transforming growth factor beta (TGF-beta) in any of its multiple isoforms, DEL-1, insulin like growth factors (IGF), placental growth factor (PLGF), hepatocyte growth factor (HGF), prostaglandin E1 (PG-E1), prostaglandin E2 (PG-E2), tumor necrosis factor alpha (TBF-alpha), granulocyte stimulating growth factor (G-CSF), granulocyte macrophage colony-stimulating growth factor (GM-CSF), angiogenin, follistatin, and proliferin, genes encoding these proteins, cells transfected with these genes, pro-angiogenic peptides such as PR39 and PR11, and pro-angiogenic small molecules such as nicotine. In one embodiment, 10-600 μg of one or a mixture of these agents may be loaded onto a stent for delivery within a vessel. These agents may have a release rate for up to eight weeks. In another embodiment, a stent may be loaded with 300 micrograms of an angiogenic agent with a release rate of eight weeks. Alternatively, a dose may be determined by those skilled in the art by conducting preliminary animal studies and generating a dose response curve. Maximum concentration in the dose response curve would be determined by the solubility of the compound in the solution.

In using drug eluting stents and related technology to deliver the vulnerable plaque treatment agent (e.g., stent 450 of FIG. 4), the active agent may be dispersed or co-dissolved directly in a solution of a matrix such as ethylene vinyl alcohol, ethylene vinyl acetate, poly(hydroxyvalerate), poly(L-lactic acid), poly(D,L-lactic acid), poly(glycolic acid), poly(lactide-co-glycolide) polycaprolactone, polyanhydride, polydiaxanone, polyorthoester, polyamino acids, poly(trimethylene carbonate), or other suitable synthetic polymers. The polymer may be coated on a stent using dip coating, spin coating, spray coating or other coating methods known in the art.

Figure 5A:
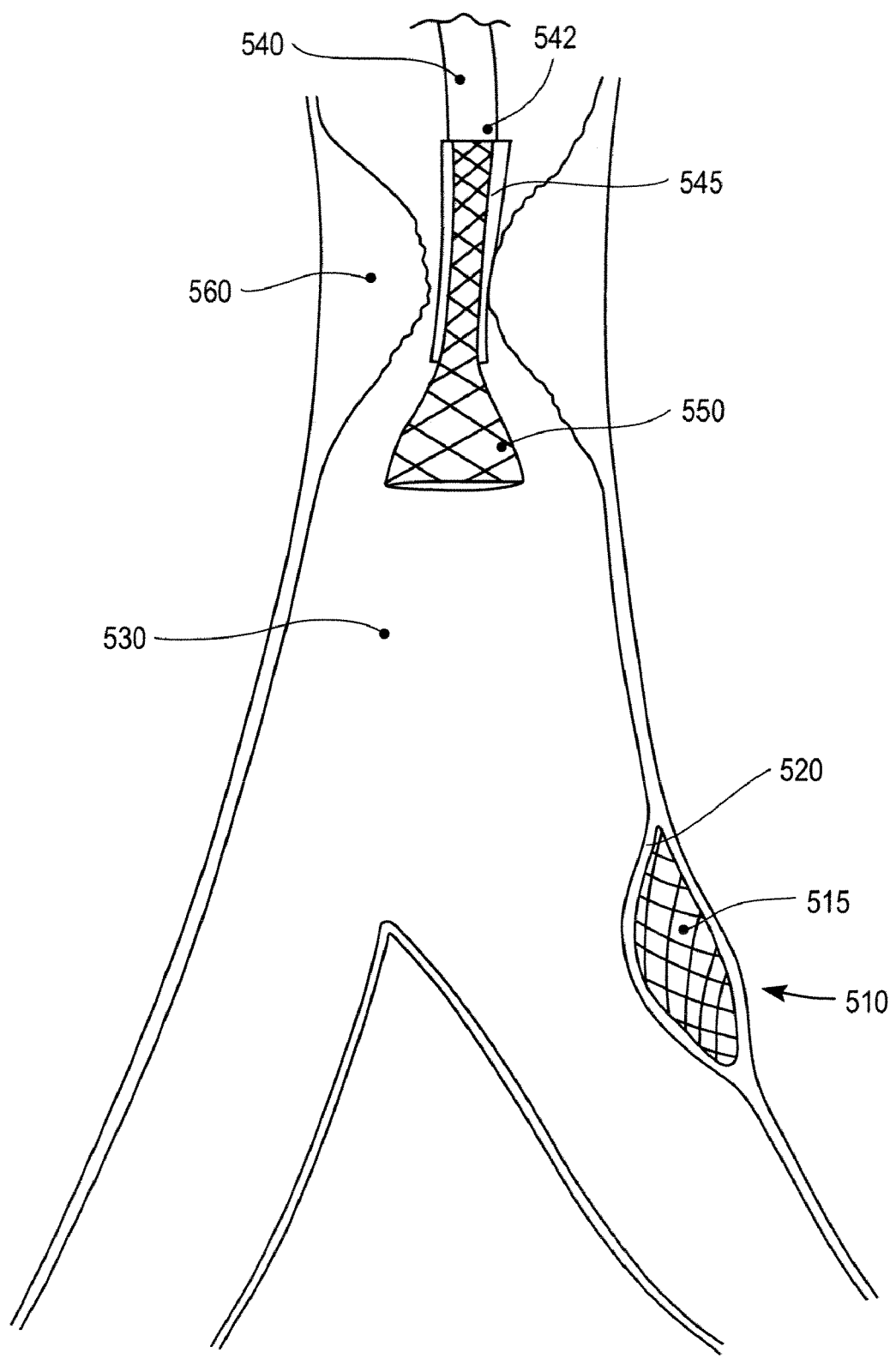
FIGS. 5A-5C illustrate an alternative embodiment of using a drug delivery stent to treat a vulnerable plaque downstream from an occlusive plaque.
Figure 5B:
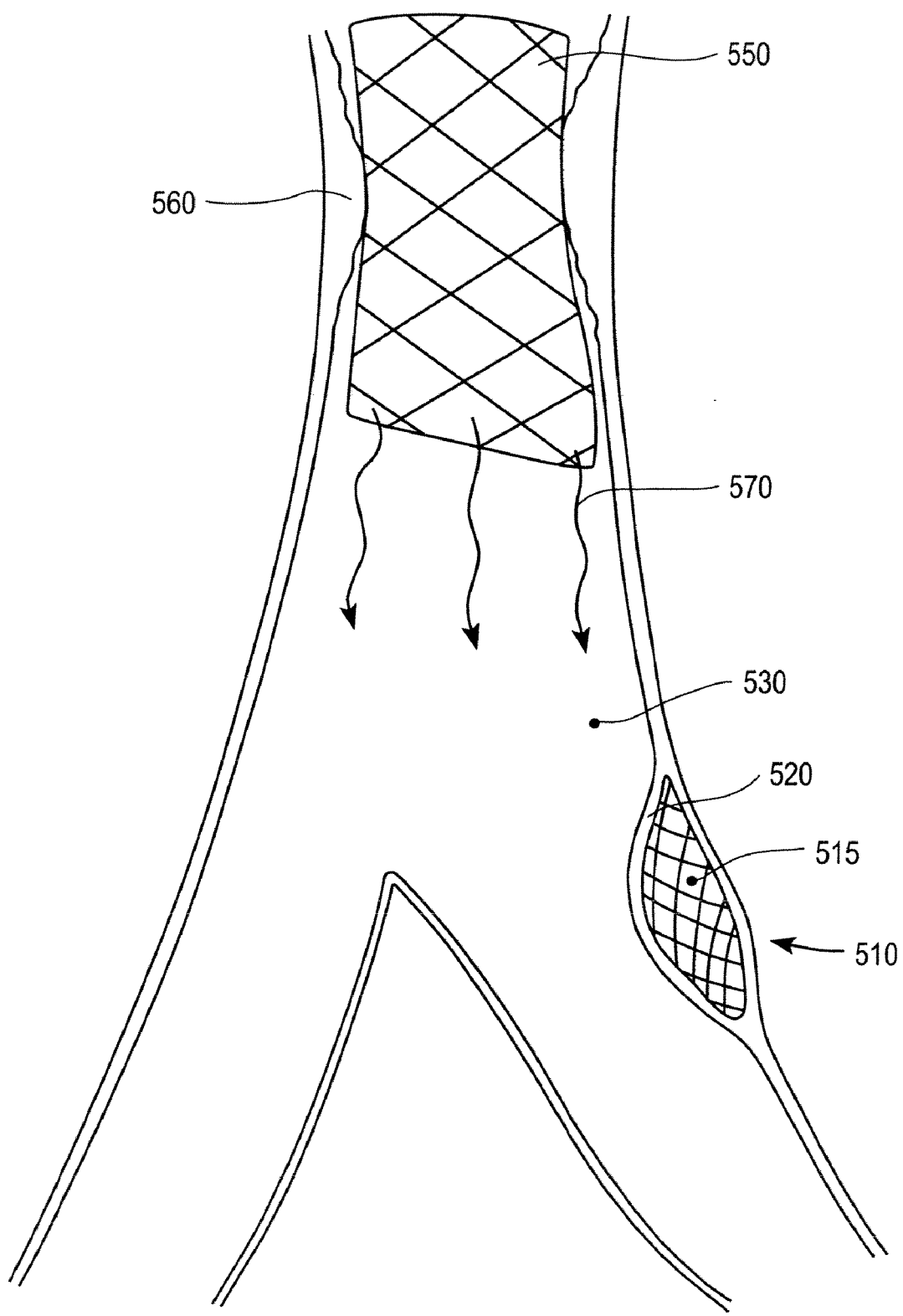
Figure 5C:
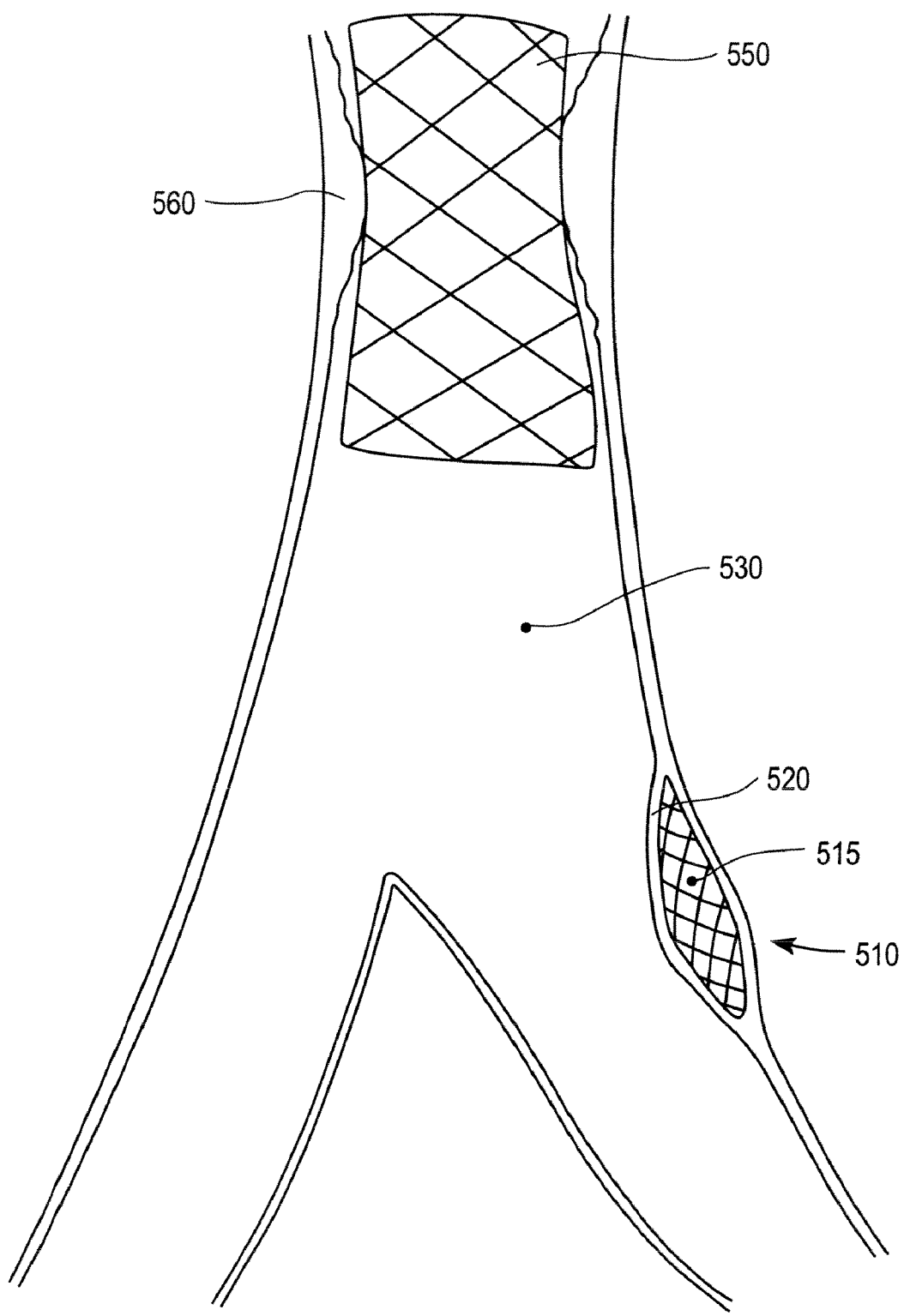

FIGS. 5A-5C illustrate the placement of drug delivery stent 550 to treat both occlusive plaque 560 and vulnerable plaque 510 localized downstream from occlusive plaque 560. In this example, vulnerable plaque 510 is located near a branched region of arterial lumen 530. In one embodiment, stent 550 is a self-expanding stent, and is disposed near distal end 542 of catheter 540. Catheter 540 is advanced through arterial lumen 530 and positioned near occlusive plaque 560. Retractable sheath 545 maintains stent 550 in a crimped and collapsed position so that stent 550 may be fit within arterial lumen 530. As illustrated in FIG. 5A, as sheath 545 retracts, stent 550 expands and applies physical pressure to occlusive plaque 560. In effect, stent 550 widens arterial lumen 530 that has been narrowed because of occlusive plaque 560. FIG. 5B illustrates stent 550 in a fully expanded position, allowing normal blood flow through arterial lumen 530.

Stent 550 may be coated with a drug or biologically active agent that releases from the surface of stent 550 when sheath 545 retracts and stent 550 becomes exposed to the blood in arterial lumen 530. The flow of the blood through arterial lumen 530 migrates the agent (as indicated by the arrows 570) towards vulnerable plaque 510. The agent targets vulnerable plaque 510. In one embodiment, the agent thickens and/or strengthens fibrous cap 520. In doing so, the likelihood of fibrous cap 520 rupturing is reduced. In another embodiment, the distribution, size or consistency of lipid core 515 is altered. A combination of agents may be utilized both to thicken fibrous cap 520 and alter the size or consistency of lipid core 515 of vulnerable plaque 510 to strengthen fibrous cap 520. FIG. 5C illustrates the treatment effects of deploying stent 550. Occlusive plaque 560 has been treated physically by compressing it against the arterial wall. Vulnerable plaque 510 has been treated through strengthening and/or thickening fibrous cap 520 and the favorable alteration of the size or distribution of the lipid core 515.

Figure 6:
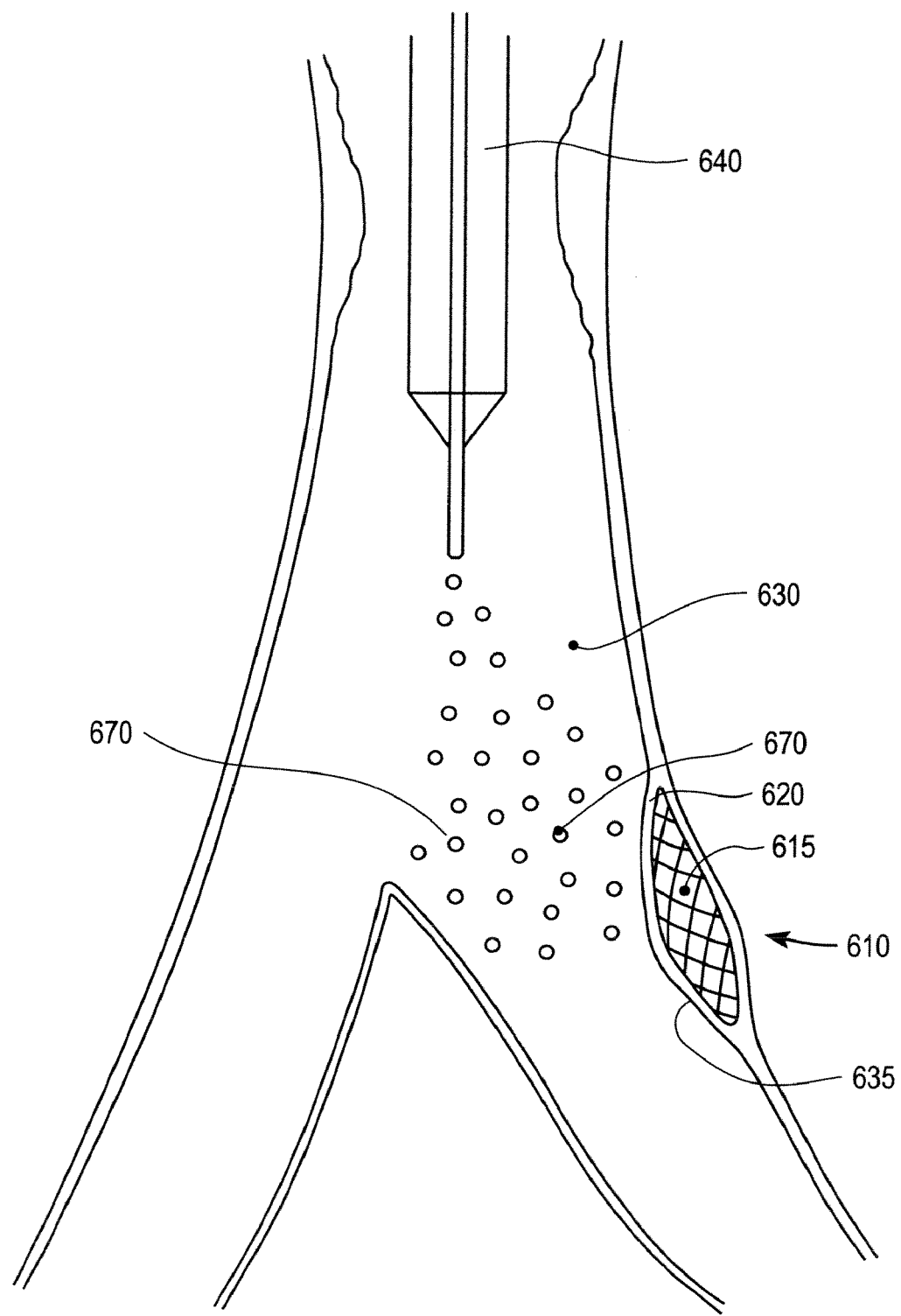
FIG. 6 illustrates one embodiment of microparticles released towards a vulnerable plaque.

A vulnerable plaque treatment agent may be delivered independent of treating occlusive atherosclerosis. FIG. 6 illustrates a vulnerable plaque treatment agent delivered in the form of a microcapsule or microparticle 670. The use of microparticle 670 allows for delivery of a treatment agent in a controlled manner to ensure treatment over a desired period of time. Some microparticles 670 possess the characteristic of being degradable at a designated rate.

Microparticles 670 may also be designed to adhere to vessel wall 635 by blending in or coating microparticles 670 with materials that promote adhesion to vessel wall 635. Microparticles 670 may be rendered bioadhesive by modifying them with bioadhesive materials such as gelatin, hydroxypropyl methylcellulose, polymethacrylate derivatives, sodium carboxymethycellulose, monomeric cyanoacrylate, polyacrylic acid, chitosan, hyaluronic acid, anhydride oligomers, polyycarbophils, water-insoluble metal oxides and hydroxides, including oxides of calcium, iron, copper and zinc. Microparticles 670 may be modified by adsorbing the bioadhesive material on microparticles 670 through ionic interactions, coating the bioadhesive material on the microparticles by dip or spray coating, conjugating the bioadhesive material to the polymer constituting microparticle 670, or blending in the bioadhesive material into the polymer constituting the microparticles 670, before the microparticles 670 are formed.

The particle size of microcapsules 670 may be less than about 10 microns to prevent possible entrapment in the distal capillary bed. Microparticles 670 may be delivered intraarterially near the site of vulnerable plaque 610, and also prophylactically at locations that are proximal and distal to vulnerable plaque 610 (not shown). Upon delivery with infusion catheter 640, microparticles 670 travel a short distance distally before adhering to vessel wall 630 near vulnerable plaque 610. The active agent of microparticles 670 is then released over time to thicken and/or strengthen fibrous cap 620, alter the size or distribution of lipid core 615, or both. Microparticles 670 may be delivered with infusion catheter 640 or any other delivery device known in the art. In one embodiment, infusion catheter may be a needle catheter having one or more injection ports to release microparticles 670.

Suitable polymers for the controlled-release microparticles 670 include, but are not limited to, poly (L-lactide), poly (D,L-lactide, poly(glycolide), poly lactide-co-glycolide), polycaprolactone, polyanhydride, polydiaxanone, polyorthoesters, polyamino acids, poly (trimethylene carbonate), and combinations thereof. Several methods exist for forming microparticles 670, including, but not limited to solvent evaporation, coacervation, spray drying, and cryogenic processing.

In solvent evaporation, the polymer is dissolved in a volatile organic solvent such as methylene chloride. The treatment agent is then added to the polymer solution either as an aqueous solution containing an emulsifying agent such as PVA, or as a solid dispersion, and stirred, homogenized or sonicated to create a primary emulsion of treatment agent in the polymer phase. This emulsion is stirred with an aqueous solution that contains a polymer in the aqueous phase. This emulsion is stirred in excess water, optionally under vacuum to remove the organic solvent and harden the microparticles. The hardened microparticles are collected by filtration or centrifugation and lyophilized.

The microparticles may also be formed by coacervation. In this method, a primary emulsion of treatment agent in an aqueous phase is formed as in the solvent evaporation method. This emulsion is then stirred with a non-solvent for the polymer, such as silicone oil to extract the organic solvent and form embryonic microparticles of polymer with trapped treatment agent. The non-solvent is then removed by the addition of a volatile second non-solvent such as a heptane, and the microparticles harden. The hardened microparticles are collected by filtration or centrifugation and lyophilized.

In spray drying, the treatment agent, formulated as lyophilized powder is suspended in a polymer phase consisting of polymer dissolved in a volatile organic solvent such as methylene chloride. The suspension then spray dried to produce polymer microparticles with entrapped treatment agent.

Microparticles may also be formed by cryogenic processing. In this method, the treatment agent, formulated as lyophilized powder is suspended in a polymer phase consisting of polymer dissolved in a volatile organic solvent such as methylene chloride. The suspension is sprayed into a container containing frozen ethanol overlaid with liquid nitrogen. The system is then warmed to −70° C. to liquefy the ethanol and extract the organic solvent from the microparticles. The hardened microparticles are collected by filtration or centrifugation and lyophilized.

Figure 13A:
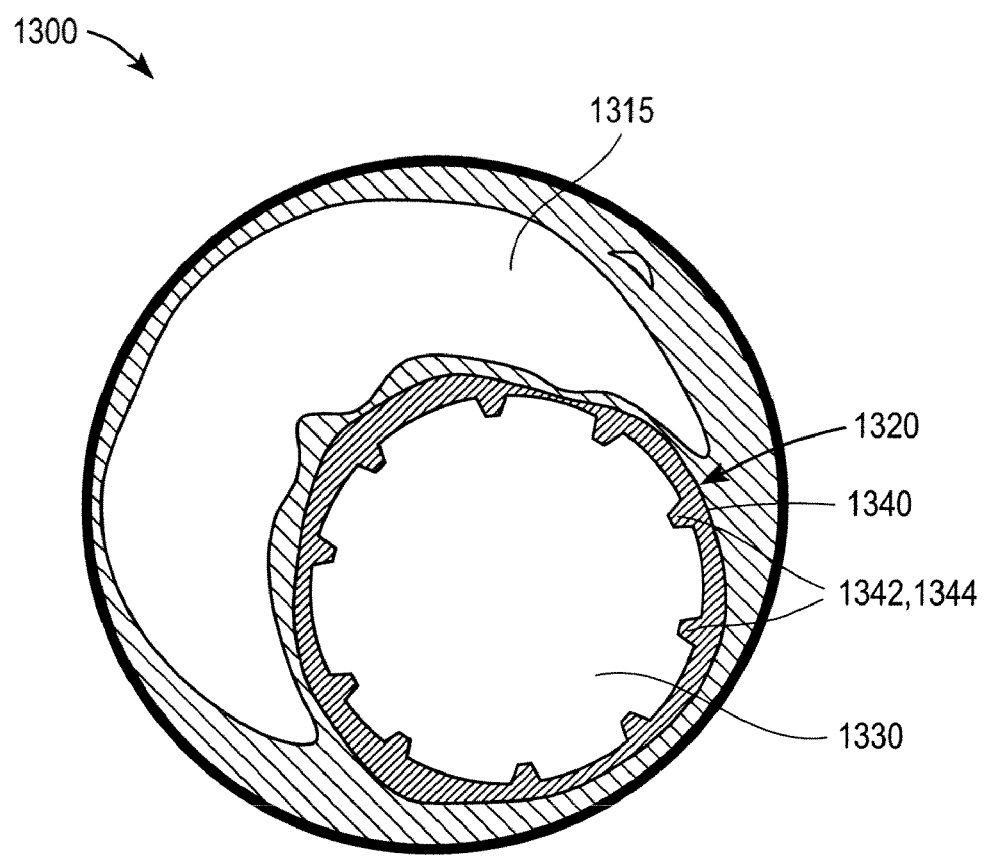
FIGS. 13A-13B illustrate cross-sectional views of one embodiment of a drug eluting stent that can be used to strengthen and to increase the thickness of the fibrous cap of the vulnerable plaque in a controlled manner.
Figure 13B:
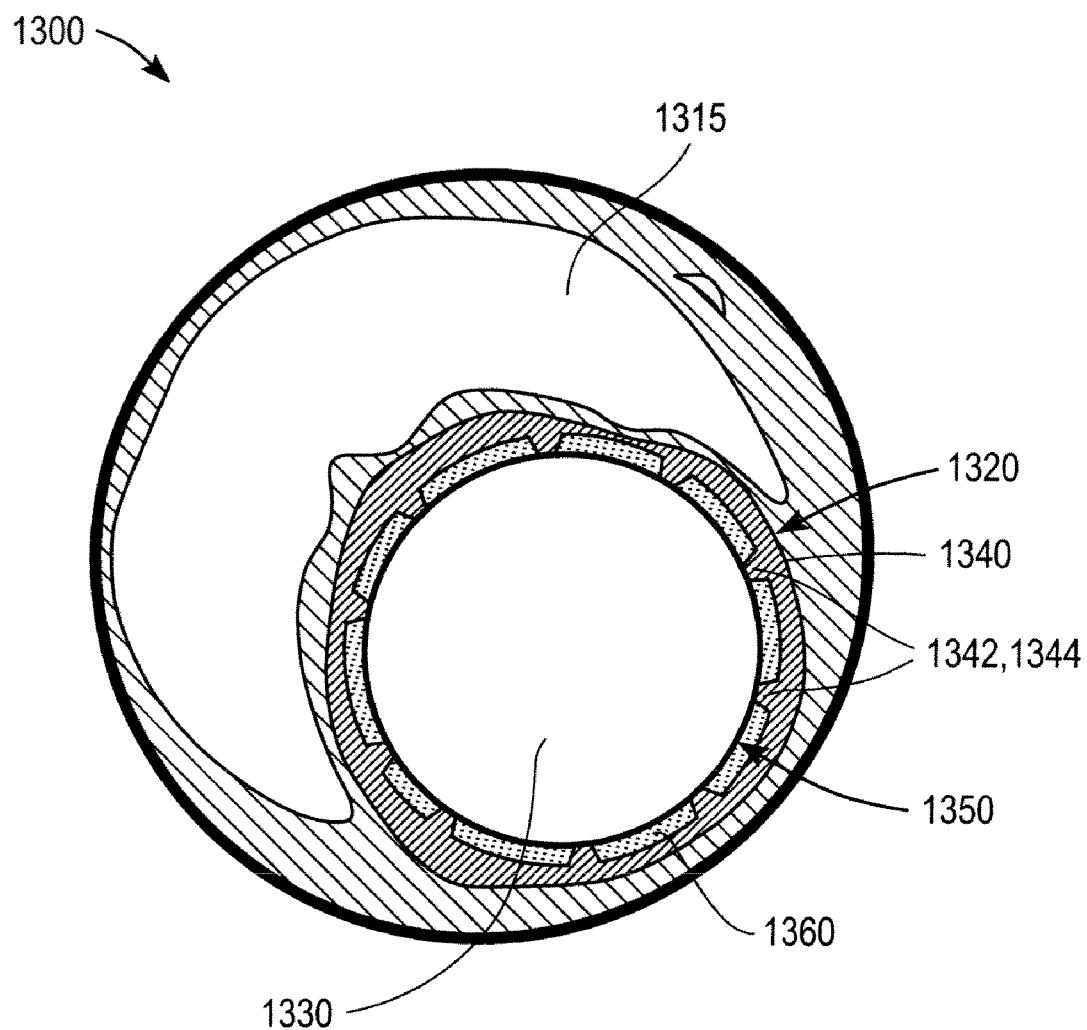

FIGS. 13A-13B illustrate cross-sectional views of one embodiment of a drug eluting stent that may be used to increase the thickness or strengthen, in a controlled manner, the fibrous cap near a vulnerable plaque. Strengthening of and increasing the thickness of the fibrous cap may redistribute and lower the stresses in the fibrous cap, effectively stabilizing the plaque and preventing its rupture.

Cross-sectional views 1300 include lumen 1330 (e.g., an arterial lumen) with lipid core 1315 of a vulnerable plaque and fibrous cap 1320. Stent 1340 having stent struts, for example struts 1342, 1344, is placed within lumen 1330 near lipid core 1315 and fibrous cap 1320. In one embodiment of using a drug eluting stent, stent 1340 serves as a vehicle for delivering an appropriate therapeutic or biologically active agent to the site of the vulnerable plaque. After stent 1340 has been deployed at a desired location, it may cause platelet deposition, fibrosis and neointimal formation in the stented region. This fibromuscular response may cause the original fibrous cap 1320 thickness to increase, thereby lowering the stresses in fibrous cap 1320 (as illustrated in FIG. 13B). This additional hyperplasia, combined with original fibrous cap 1320 produced by stent 1340 can be thought of as a "neo-cap." Neo-cap 1360, as illustrated in FIG. 13B, has developed near the inner diameter of stent 1340. The controlled release of a drug or biologically active agent from stent 1340 may allow an increase in fibrous cap 1320 thickness because of the injury sufficient to stabilize lipid core 1315, but may minimize or prevent excessive restenosis. The type of biologically active agent, the dosage, release rate and the duration of release may influence the growth of neo-cap 1360. Therefore, by controlling these factors the growth of neo-cap 1360 may be controlled. After the thickness of fibrous cap 1320 has been increased and lipid core 1315 has been stabilized, the size of lumen 1330 may be increased by balloon angioplasty if necessary.

The biologically active agent used for controlling fibrous cap 1320 growth may be delivered using a metal stent platform (e.g., stent 1340). The drug may be released through a polymer membrane-matrix system that is deposited on the surface of the stent. Polymers such as EVAL can be used for the membrane-matrix system. Several choices of metals are available for making the stent, including but not limited to, stainless steel, cobalt-chromium alloy and shape-memory alloys such as Nitinol. Depending on the design of the stent and delivery system, it may be possible to direct the biologically active agent to act in specific locations of interest in the vulnerable plaque. For example, biologically active agents which are anti-inflammatory in nature may be optimally delivered into or around the plaque shoulder regions, a site of inflammatory cell accumulation where the lipid core edges meet the normal wall opposite the vulnerable plaque. Conversely, it may be possible to direct the biologically active agent away from specific locations of interest in the vulnerable plaque. For example, biologically active agents which are anti-restenotic, such as Actinomycin-D, may be directed to act away from the expected regions of high stress in fibrous cap 1320, which cover lipid core 1315 in general. These regions would be the shoulder regions or the portion of fibrous cap 1320 centered circumferentially along lipid core 1315 edge nearest lumen 1330. And finally, it may also be possible to design stent 1340 or other types of delivery systems that selectively diffuse a biologically active agent appropriately, by leveraging through stent 1340 design the stress-assisted diffusion properties at the stent-plaque interface in these select regions.

The biologically active agent may also be delivered using a biodegradable polymeric stent. In this case, after the biologically active agent has eluted from the stent, the stent degrades within a certain period of time leaving behind a stabilized plaque. The polymers available for making the stent include poly-L-lactide, polyglycolic/poly-L-lactic acid (PGLA), Poly-L-latic acid (PLLA), poly-L-lactide, polycaprolactone (PCL), poly-(hydroxybutyrate/hydroxyvalerate) copolymer (PHBV) or shape memory polymers such as a compound of oligo($\epsilon$-caprolactone) dimethacrylate and n-butylacrylate.

Examples of therapeutic or biologically active agents include but are not limited to rapamycin, actinomycin D (ActD) and their derivatives, antiproliferative substances, antineoplatic, antinflammatory, antiplatelet, anticoagulant, antifebrin, antithrombin, antimitotic, antibiotic and antioxidant substances. Examples of antineoplastics include taxol (paclitaxel and docetaxel). Examples of antiplatelets, anticoagulants, antifibrins and antithrombins include sodium heparin, low molecular weight heparin, hirudin, IIb/IIIa platelet membrane receptor antagonist and recombinant hirudin. Examples of antimitotic agents include methotrexate, azathioprine, vincristine, vinblastine, fluororacil, adriamycin and mutamycin. Examples of cytostatic or antiproliferative agents include angiopeptin, calcium channel blockers (such as Nifedipine), Lovastatin (an inhibitor of HMG-COA reductase, a cholestrol lowering drug from Merck). Other therapeutic or biologically active agents which may be utilized include alpha-interferon, genetically engineered epithelial cells and dexamethasone. Dosages comparable to that described above with respect to drug eluting stents may be used.

Stent Grafts

In one embodiment, a stent graft may be used for the treatment of vulnerable plaque. The stent graft may have a thin, expandable polytetrafluoroethylene (ePTFE) cylindrical tube affixed to an inner surface of a self-expandable stent. The inner surface of the ePTFE tube may have a layer of endothelial cells. The endothelial cells, when dispersed near the vulnerable plaque region, may promote cell migration to form a fully lined monolayer on the lumen surface. The stent graft may also shield existing vulnerable plaque from the possibility of an acute, thrombotic event. If the plaque ruptures, a cascade of blood-vessel wall interactions occurs, resulting in thrombosis and ultimately partial or total arterial occlusion. Therefore, shielding vulnerable plaque from the vessel lumen would eliminate the possibility of plaque contents being exposed to blood flow in case of rupture. In addition, the stent graft may provide reinforcement to the fibrous cap and reduce any physical stress placed on it due to the size of the lipid core.

Figure 7:
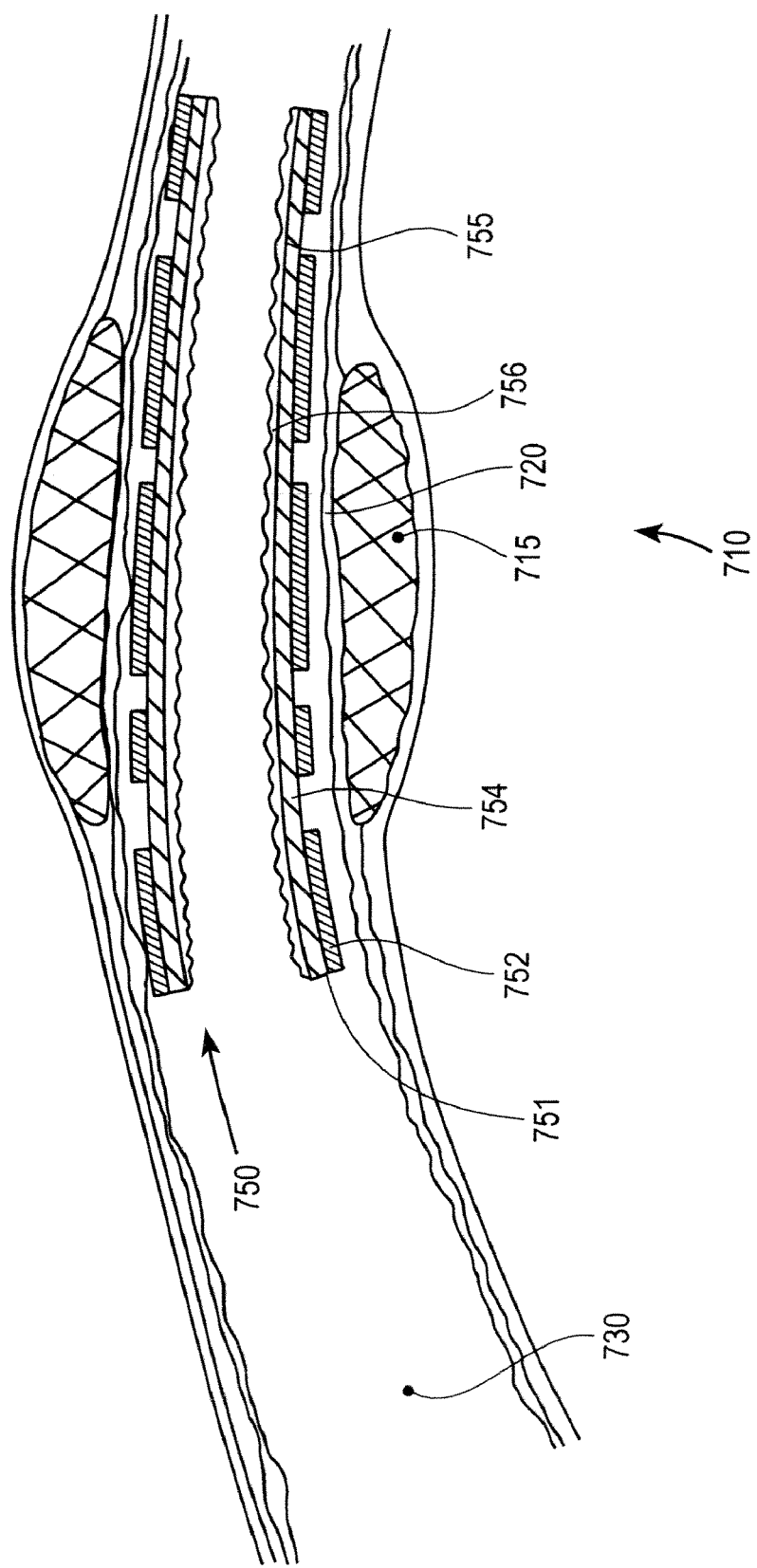
FIG. 7 illustrates one embodiment of a stent graft used to treat a vulnerable plaque.

FIG. 7 illustrates another embodiment for treating vulnerable plaque in which stent graft 750 is deployed near vulnerable plaque 710. Stent graft 750 has a thin expandable polytetrafluoroethylene (ePTFE) cylindrical tube 754 affixed to inner surface 751 of self-expandable stent 752. Inner surface 755 of ePTFE tube 754 has a layer of endothelial cells 756. The layer of endothelial cells 756 promotes cell migration that eventually forms a complete monolayer on the surface of arterial lumen 730. As such, stent graft 750 shields existing vulnerable plaque 710 from an occlusive thrombosis event. Moreover, stent graft 750 may provide reinforcement to fibrous cap 720 and reduce any increased physical stress placed on it in vivo due to lipid core 715 presence or other hemodynamic forces.

ePTFE tube 754 serves as a physical barrier between vulnerable plaque 710 and arterial lumen 730. Because ePTFE lumen surface 755 acts as an arterial equivalent, ePTFE tube 754 should remain free from occlusion. In one embodiment, the ePTFE tube 754 is made anti-thrombotic by surface treatment. The surface of ePTFE tube 754 may be made anti-thrombotic for use as a vascular graft by seeding surface 755 with endothelial cells 756. Endothelial cells 756 seeded within vascular grafts have been shown to promote cell migration that eventually form a fully lined monolayer on a lumen surface.

Several approaches exist to seed stent graft 750 with endothelial cells 756. In one embodiment, a pressurized sodding technique may be used in which ePTFE tube 754 is expanded to 5 psi using media that contain endothelial cells. Endothelial cells 756 are isolated from the canine falciform ligament fat. Endothelial cells may also be isolated from human liposuction fat micro-vessel, umbilical veins, and other comparable sources.

Stent graft 750 may be disposed near a target vulnerable plaque 710 in a manner similar to that of a drug eluting stent 450, 550 at an occlusive site discussed above (e.g., with respect to FIGS. 4 and 5A-5C). Stent graft 750 is disposed near a distal end of a catheter (not shown). The catheter is passed through arterial lumen 730 so that stent graft 750 is positioned near vulnerable plaque 710. A retractable sheath (not shown) maintains the stent graft in a crimped position so that the stent graft may be advanced within arterial lumen 730. As illustrated in FIG. 7, stent graft 750 expands and applies physical pressure to fibrous cap 720 surrounding vulnerable plaque 710. FIG. 7 illustrates stent graft 750 in a fully expanded position, allowing normal blood flow through arterial lumen 730.

Figure 8A:
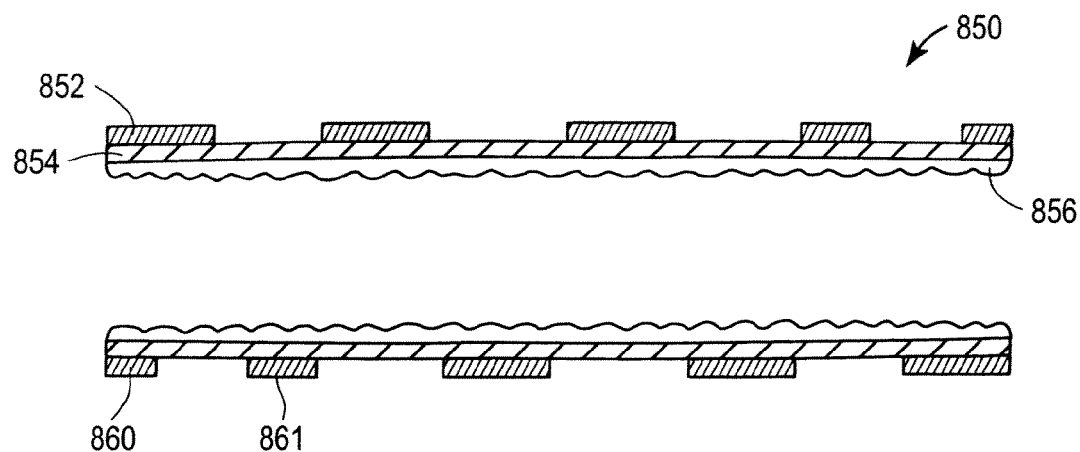
FIGS. 8A-8B illustrate cross-sectional views of a stent graft.
Figure 8B:
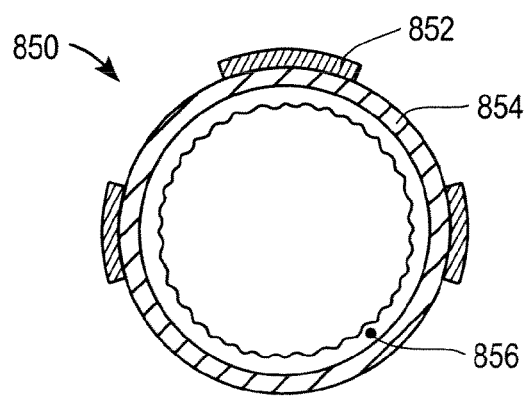

FIGS. 8A-8B illustrate cross-sectional views of stent graft 850 having inner tube 854 lined with endothelial cells 856 for treating vulnerable plaque. A self-expandable stent 852 is used as structural support to keep stent graft 850 secured in place within arterial lumen 730. A self-expandable stent may be advantageous over a balloon expandable stent. A self-expandable stent does not require an internal lumen pressure to expand, and so any seeded cells 856 are kept intact. In contrast, a balloon expandable stent could damage cells 856 of stent graft 850 when expanded. The self-expanding stent 852 may be made from a shape memory alloy such as NiTi (e.g., Nitinol). In order to provide additional flexibility to stent 852, stent links (e.g., 860, 861) may be eliminated from stent 852. In an alternative embodiment, stent 852 may have a series of shape memory metallic rings (not shown) bonded to the outer surface of ePTFE tubing 854.

Various techniques are available to bond ePTFE tube 854 to stent 852. For example, to bond the ePTFE tube to the metal, a primer is first applied to the metallic portions (e.g., 860, 861) of stent 852. These rings are then inserted over ePTFE tube 854. Silicon adhesive is used to bond metallic rings 860, 861 to ePTFE tubing 854. The stent graft is cured at about 150° C. for approximately 15 minutes. The silicon adhesive seeps through the ePTFE tube matrix and after curing acts as a medium that mechanically fastens the ePTFE tube to the metal. The inner surface of the polymeric tube is then seeded with endothelial cells.

In addition to the shape memory alloys, stent rings 860, 861 may also be made from shape memory polymers. Various shape memory polymers with great potential for biomedical applications are currently in the research phase. For example oligo(e-caprolactone) dimethacrylate and n-butyl acrylate are two monomeric compounds that, when combined, generate a family of polymers that exhibit excellent shape memory characteristics. The oligo(e-caprolactone) dimethacrylate furnishes the crystallizable "switching" segment (characteristic of shape memory materials) that determines both the temporary and permanent shape of the polymer. By varying the amount of the comonomer, n-butyl acrylate, in the polymer network, the cross-link density can be adjusted. This allows the mechanical strength and transition temperature of the polymers to be tailored over a wide range. Therefore, the stent incorporating these polymers can be deployed using their shape memory characteristics. Furthermore, other polymers such as polyurethane and ultra high molecular weight polyethylene (UHMWPE) can also be used for tubing used in the stent graft.

In an alternative embodiment, stent graft 850 may also be used as an apparatus for local drug delivery. Stent graft 850 may be loaded with anti-restenotic, anti-thrombotic, or other vulnerable plaque treatment agents (e.g., as discussed above with respect to FIGS. 4 and 5A-5C). Furthermore, in yet another alternative embodiment, stent graft 850 may be radioactively enhanced or incorporated with a material that generates a magnetic susceptibility artifact of stent graft 850.

Needle Catheter

In another embodiment, a vulnerable plaque treatment drug or biologically active agent may be injected through or around a vulnerable plaque region. In one embodiment, a needle catheter may be used to inject the biologically active agent. The needle catheter may be adjusted to penetrate various targets around the vulnerable plaque including, but not limited to: fibrous cap, proteoglycan-rich surface layer, subintimal lipid core, proximal or distal regions of the vulnerable plaque, media containing smooth muscle cells around the lipid core, and the periadventitial space.

In an alternative embodiment, the needle catheter may include sensing capabilities to determine the depth of penetration of the needle, as well as dial-in needle extension. Furthermore, different angle balloons may be added in order to use case-specific ramp angle to penetrate into the vulnerable plaque region while positioning the needle catheter below the actual occlusion. The needle catheter may be placed proximal or distal to the vulnerable plaque region because studies have shown cell localization, activity, and apoptosis have preferential occurrence in the upstream or downstream parts of vulnerable plaque regions.

Figure 9A:
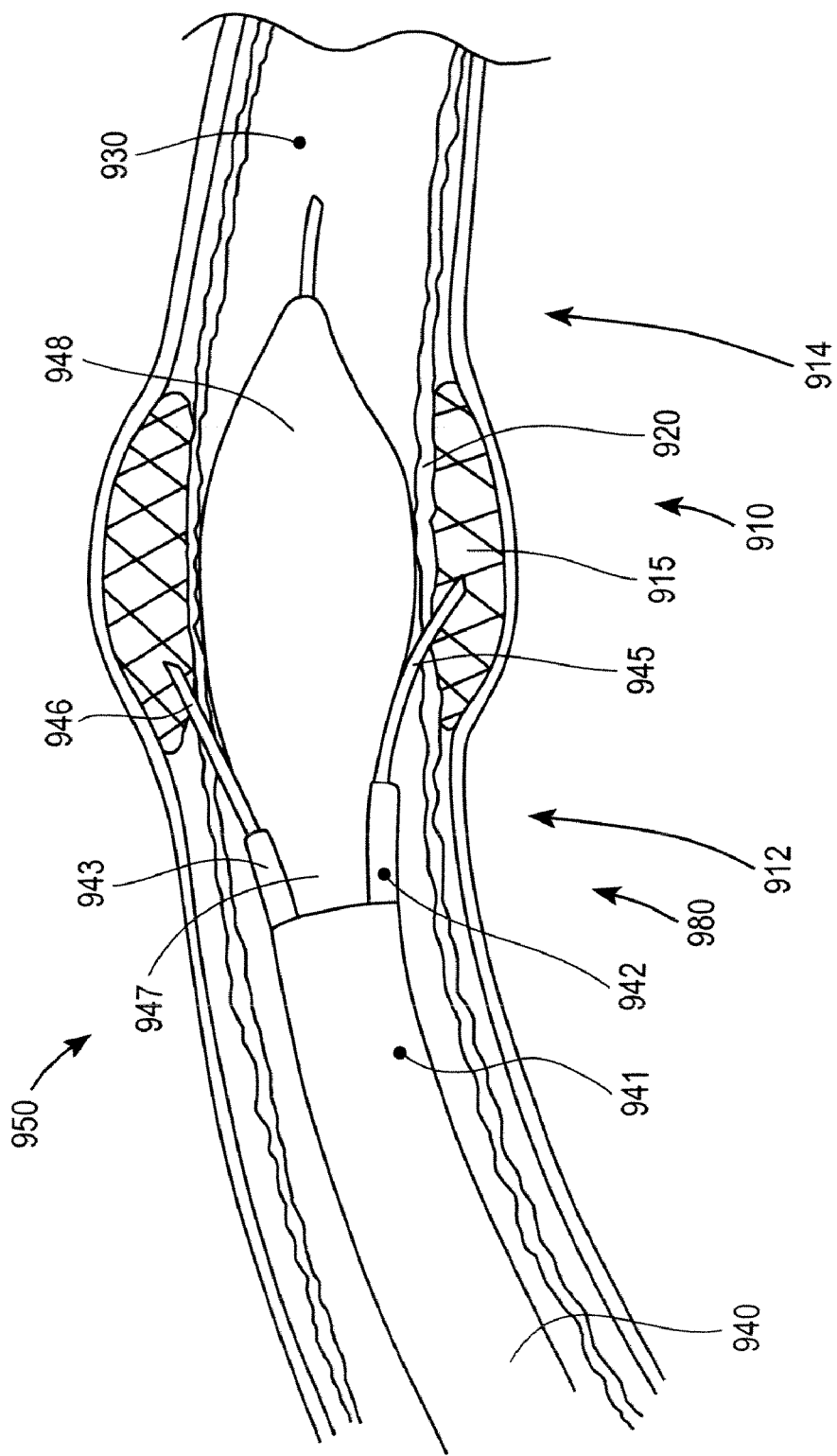
FIGS. 9A-9D illustrate various embodiments of using a needle catheter to treat a vulnerable plaque.

FIG. 9A illustrates a cross-sectional view of one embodiment of needle catheter 950 that may be used to inject a vulnerable plaque treatment agent into arterial wall 980 near vulnerable plaque 910. Vulnerable plaque 910 has developed within arterial wall 980, separated from arterial lumen 930 by fibrous cap 920. Distal end 941 of catheter 940 has inflatable balloon 948 with at least one needle lumen 945 extending from distal end 941 of catheter 940 along proximal end 947 of balloon 948. Retractable needle 945 extends from needle lumen 942 and penetrates arterial wall 980. Inflated balloon 948 secures needle catheter 950 at a target location. Moreover, because needle sheath 942 is coupled along proximal end 947 of balloon 948, inflated balloon 948 provides a penetration angle for needle 945. Needle catheter 950, as illustrated, has two needles 945, 946 extending from distal end 941 of catheter 950. Any number of needles may be utilized with needle catheter 950. For example, in an alternative embodiment, the needle catheter may have only one needle for injecting a vulnerable plaque treatment agent.

As illustrated, needle catheter 950 targets lipid core 915 of vulnerable plaque 910 directly. In one embodiment, a lipid lowering agent may be injected into vulnerable plaque 910, or agents which could change lipid core properties could be injected. PEG with an aldehyde/gluteraldehyde mix may be injected into lipid core 915 potentially cross-linking vulnerable plaque 910 components to inhibit erosion, rupture, or other forms of destabilization. Other vulnerable plaque treatment agents may be used, including antioxidants, and extracellular matrix synthesis promoters (e.g., as discussed with respect to FIGS. 4 and 5A-5C).

Needle catheter 950 may also be configured to include a feedback sensor (not shown) for mapping the penetration depth of needles 945, 946. The use of a feedback sensor provides the advantage of accurately targeting the injection location. Depending on the type of treatment agent used and treatment desired, the target location for delivering the treatment agent may vary. For example, it may be desirable to inject a drug near fibrous cap 920 or media 984 of arterial wall 980. Alternatively, it may be desirable to inject a drug into lipid core 915, or adventitia 986.

In use, distal end 941 of needle catheter 950 is inserted into the lumen of a patient and guided to a vulnerable plaque region. As illustrated in FIG. 9A, distal end 941 of needle catheter 950 is positioned near a proximal end 912 of vulnerable plaque 910. Alternatively, needle catheter 950 may be positioned near a distal end 914 of vulnerable plaque 910. Vulnerable plaque 910 may be detected using the sensor (not shown) disposed on needle catheter 950. By utilizing a sensor, the injection site for treating vulnerable plaque 910 may be precisely identified.

Figure 10A:
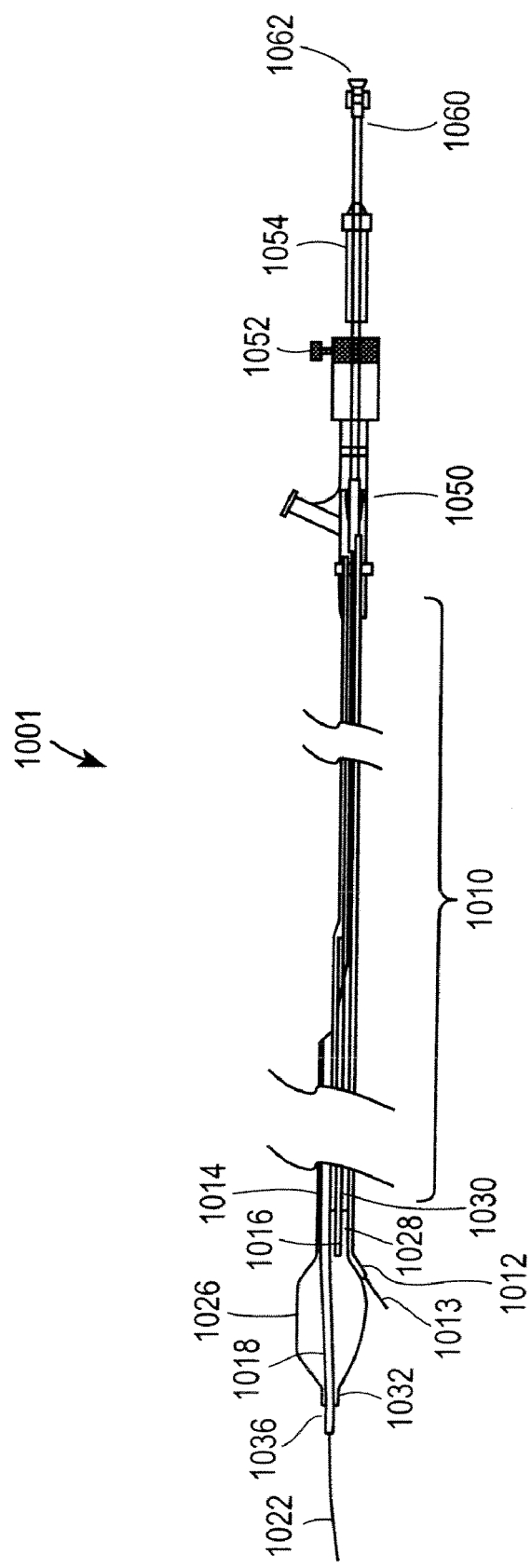
FIGS. 10A-10B illustrate one embodiment of a needle catheter.
Figure 10B:
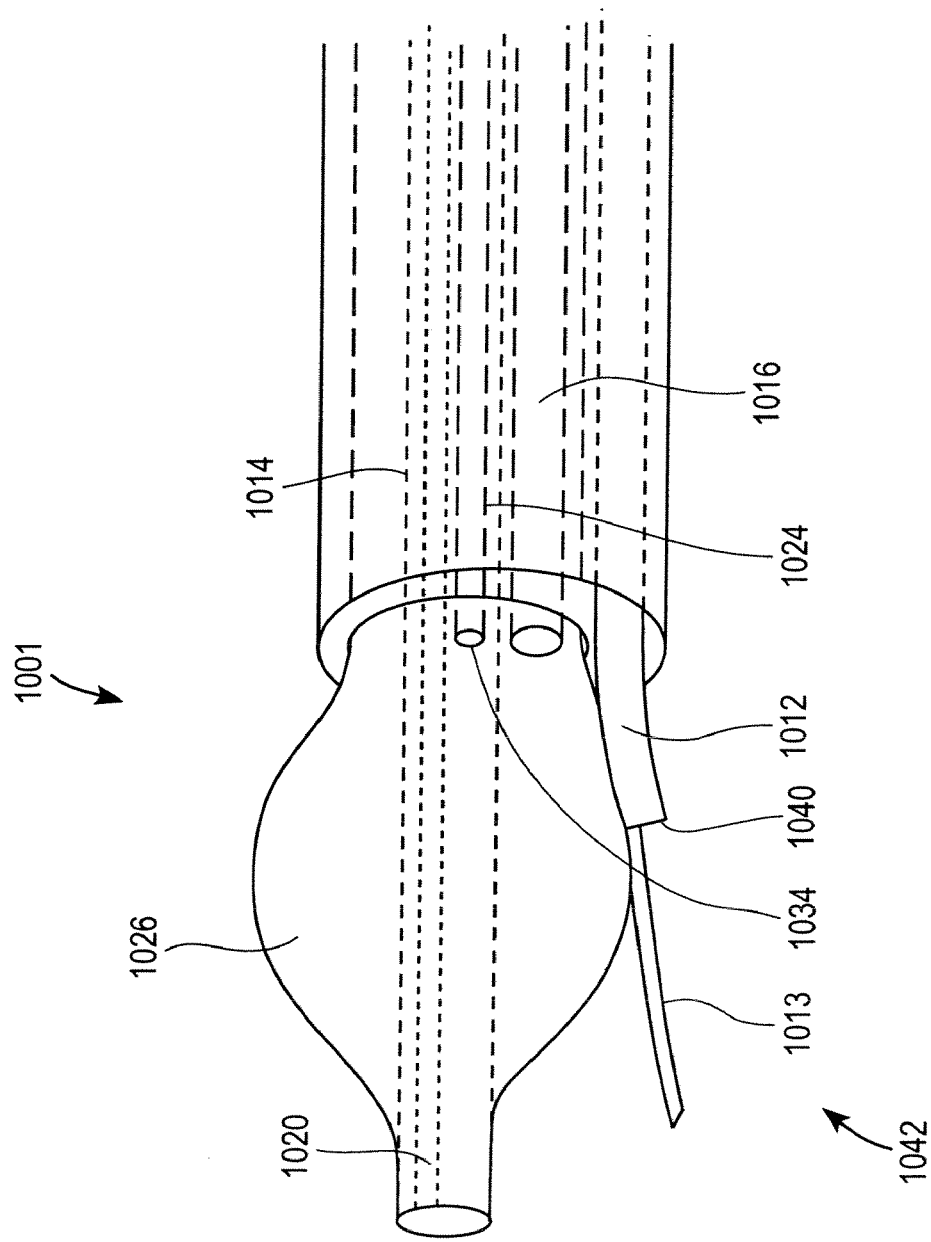

FIGS. 10A and 10B illustrate cross sectional views of one embodiment of a needle catheter for injecting a vulnerable plaque treatment drug or biological agent. FIG. 10 illustrates needle catheter 1001 with sensing capabilities having elongated catheter body 1010 that surrounds needle lumen 1012 and inner lumen 1014. Housed within inner lumen 1014 are fluid lumen 1016 and inner member 1018 that also contains guide wire 1020, guide wire lumen 1022, and ultrasonic element lumen 1024. Inflatable balloon 1026 is coupled to inner lumen 1014 and the inner member 1018. Proximal end 1028 of balloon 1026 is coupled to distal end 1030 of inner lumen 1014 and distal end 1032 of balloon 1026 is coupled to distal end 1036 of inner member 1018.

In an alternative embodiment, both guide wire 1022 and retractable ultrasonic element 1034 may be housed within inner member 1014. Elongate body 1010 surrounds inner member 1014 and needle lumen 1012. Housed within inner lumen 1014 are inner member 1018 and fluid lumen 1016. Inner member 1018 surrounds guide wire 1022 and retractable ultrasonic element 1034. Inflatable balloon 1026 is coupled to inner lumen 1014 and inner member 1018. Proximal end 1028 of balloon 1026 is coupled to distal end 1030 of inner lumen 1014 and distal end 1032 of balloon 1026 is coupled to distal end 1036 of inner member 1018.

The ultrasonic element lumen 1024 of inner member 1018 houses retractable ultrasonic element 1034. The distal end of the ultrasonic element has an ultrasound transducer or transducer array and the proximal end contains the associated co-axial cable that connects to an imaging display system (not shown). Ultrasonic waves generated by the ultrasonic element impinge on the surface of a vulnerable plaque or vulnerable plaque region. The timing/intensity of the ultrasonic waves reflected back to the transducer differentiates between the various anatomic boundaries or structures of the vulnerable plaque region, for example, the various layers of an arterial wall. The waves detected by the transducer are converted to electric signals that travel along the coaxial cable to the imaging system. The electrical signals are processed and eventually arranged as vectors based on the digitized data. In one embodiment, the ultrasound transducer has piezoelectric crystal configured for optimal acoustic output efficiency and energy conversion. In alternative embodiments, the crystal is made of PZT or lead-ceramic materials such as $PbTiO_3$ (lead titanate) or $PbZrO_3$ (lead zirconate).

As further illustrated in FIGS. 10A-10B, retractable needle 1013 is housed in needle lumen 1012 and freely movable therein. The hollow, tubular shaped needle 1013, having an inner diameter within a range of approximately 0.002 inch to 0.010 inch ($5.1 \times 10^{-3}$ cm to $25.4 \times 10^{-3}$ cm) and an outer diameter within the range of approximately 0.004 inch to 0.012 inch ($10.2 \times 10^{-3}$ cm to $30.5 \times 10^{-3}$ cm), provides a fluid channel that extends from proximal end 1040 to distal end 1042 of needle 1013. Distal end 1042 of needle 1013 has a curved tip. In one embodiment, needle 1013 has an angle of curvature of about 30 degrees to 90 degrees. The curvature of needle 1013 facilitates placement of the needle tip near or within a desired target of a vulnerable plaque region. Needle 1013 may be formed from a variety of metals including, but not limited to stainless steel, NiTi (nickel titanium) (e.g., Nitinol) or other comparable semi-rigid materials.

Proximal end 1040 of needle 1013 is coupled to adapter 1050 that couples needle 1013 to needle lock 1052 and needle adjustment knob 1054. Needle lock 1052 is used to secure needle 1013 in place and prevent further movement of needle 1013 within an arterial lumen once needle 1013 is placed in the target position. Needle adjustment knob 1054 controls accurate needle extension out of the distal end of the catheter and depth of penetration into the vulnerable plaque region. As such, movement of needle adjustment knob 1054 moves needle 1013 in and out of needle lumen 1012. Once needle 1013 has penetrated a target to a desired depth, needle lock 1052 enables needle 1013 to be secured in place thereby preventing any movement of needle 1013 within needle lumen 1012.

A drug injection port 1060 is disposed near proximal end 1062 of needle catheter 1001. Drug injection port 1060 couples needle catheter 1001 with various dispensing devices such as a syringe or fluid pump. Fluids injected into drug injection port 1060 travel through needle 1013 and are dispensed from the distal tip of needle 1013.

Figure 9B:
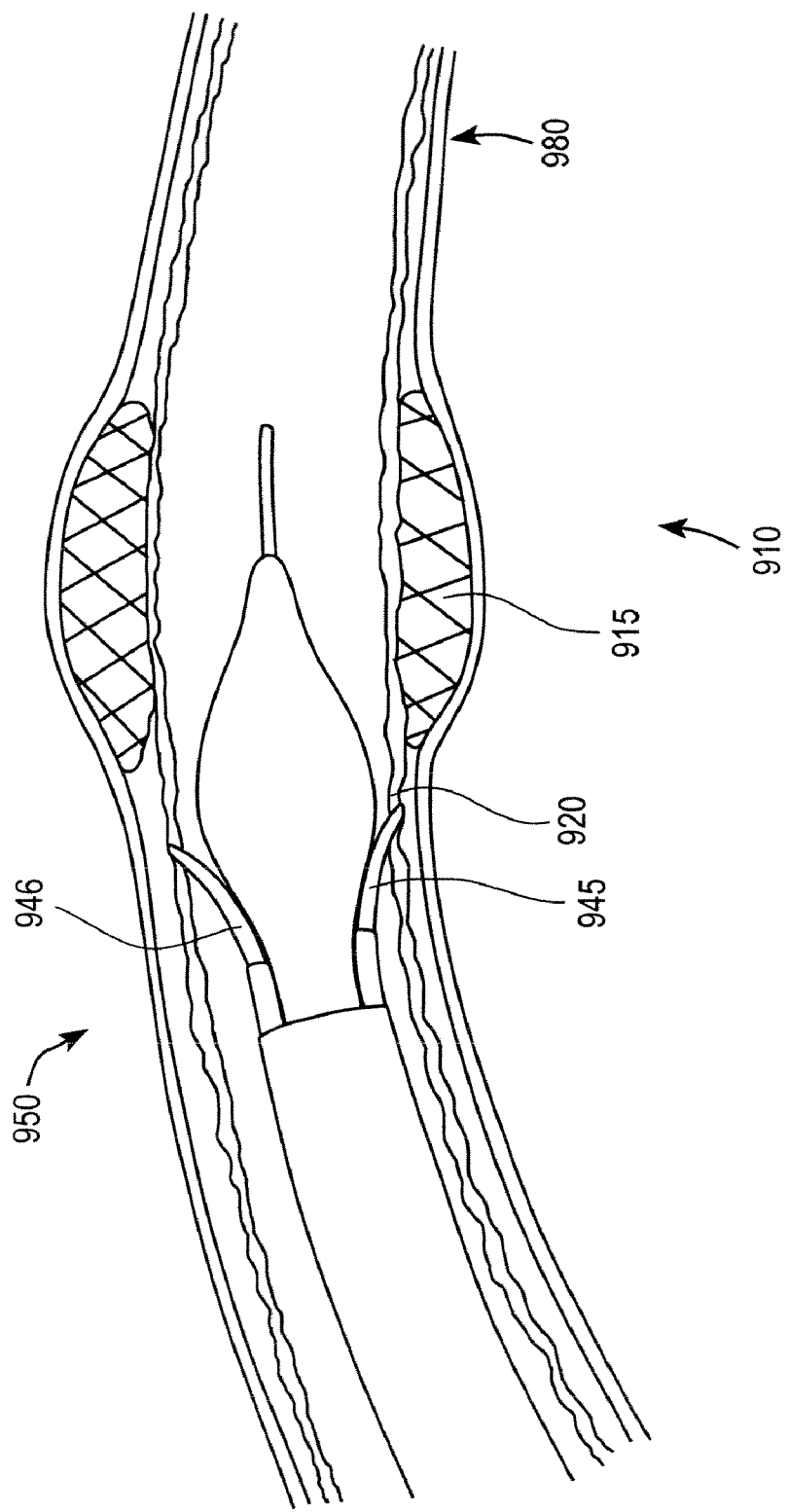
Figure 9C:
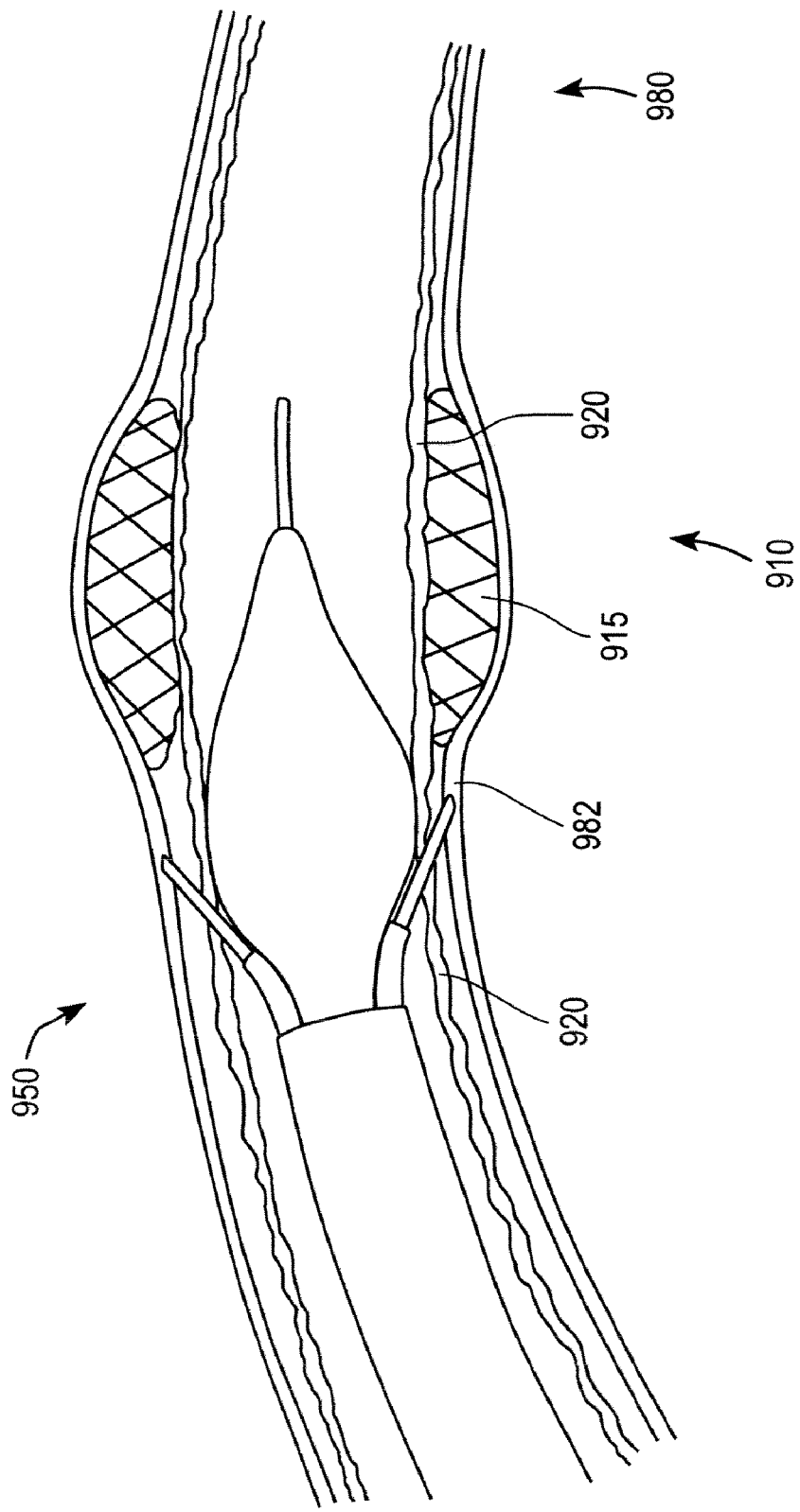
Figure 9D:
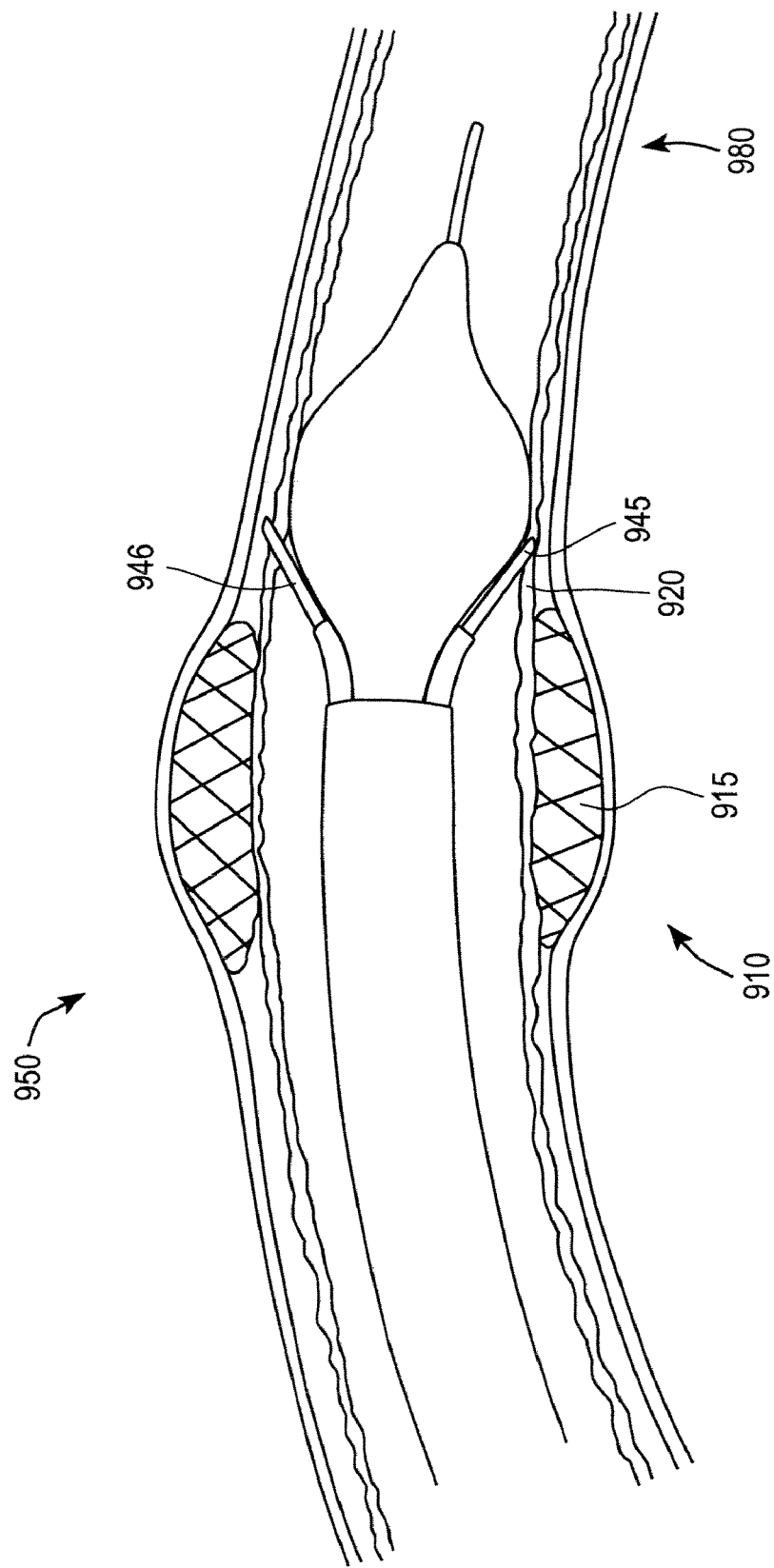

FIGS. 9B-9D illustrate embodiments of needle catheter 950 targeting various regions near a vulnerable plaque for injection of a vulnerable plaque treatment agent. As discussed above, needle catheter 950 may have a feedback sensor (e.g., ultrasonic element 1034 of FIG. 10B) to determine and control a penetration depth for needles 945, 946. The sensor provides the advantage of accurately targeting a desired injection site. As such, needle catheter 950 may inject a vulnerable plaque stabilizing drug or biologically active agent into fibrous cap 920 as illustrated in FIG. 9B, regions within the subintimal space 982 of arterial wall 980 as illustrated in FIG. 9C, or regions distal to vulnerable plaque 910 as illustrated in FIG. 9D.

For example, with respect to FIG. 9B antioxidants such as reactive oxygen scavengers (ROS), vitamin C and E may be injected into fibrous cap 920. The oxidant acts as a matrixase inhibitor to prevent significant collagen degradation within fibrous cap 920.

In another embodiment, needle catheter 950 may also be used as part of a biological or gene therapy method to treat vulnerable plaque 910. For example, upregulators of tissue inhibitors of metalloproteinases (TIMPS) may be injected into adventitia 986. TIMPS are expressed by surrounding smooth muscle cells to downregulate MMP production. Alternatively, recombinant TF pathway inhibitors (TFPI) may one day be injected into lipid core 915 to inhibit thrombosis due to erosion, rupture or other forms of plaque destabilization.

In yet another embodiment, needle catheter 950 may be used to deliver an agent to induce angiogenesis and/or arteriogenesis as described above with respect to FIG. 12. The therapeutic angiogenesis agents and drugs discussed above may be injected near a treatment site as an alternative to delivery by a drug eluting stent.

FIGS. 11A-11D illustrate flowcharts describing methods for stabilizing vulnerable plaque. The methods described with respect to FIGS. 11A-11D include detecting vulnerable plaque. Various techniques may be utilized to detect the presence and location of vulnerable plaque. For example, an ultrasound probe (IVUS) or an optical coherence tomography probe (OCT) may be guided through the arteries to scan for vulnerable plaque. Alternatively, magnetic resonance imaging (MRI) devices may be able to detect vulnerable plaque. Near Infrared spectroscopy is another technique for detecting vulnerable plaque. For example, certain wavelengths of light penetrate the arterial wall and produce a specific chemical signature that could correlate to vulnerable plaque composition. Additionally, thermography may also be used to detect vulnerable plaque. Plaques that rupture tend to be inflamed, and data indicates this correlates to a higher temperature compared to non-vulnerable type plaques that do not rupture. As such, a temperature sensitive probe that measures the temperature of arteries could indicate the presence of vulnerable plaque. Alternatively, liquid crystal thermography methods may also be used. For example, a balloon material made of a thermochromic liquid crystal material may be able to optically detect property changes when exposed to increases in temperature. When the balloon contacts a vulnerable plaque, the higher temperature of the vulnerable plaque may be detected by analyzing a beam of light directed towards the suspected vulnerable plaque region and the balloon material in contact therewith. The light may undergo a color change in the balloon material as a result of the higher temperature.

Figure 11A:
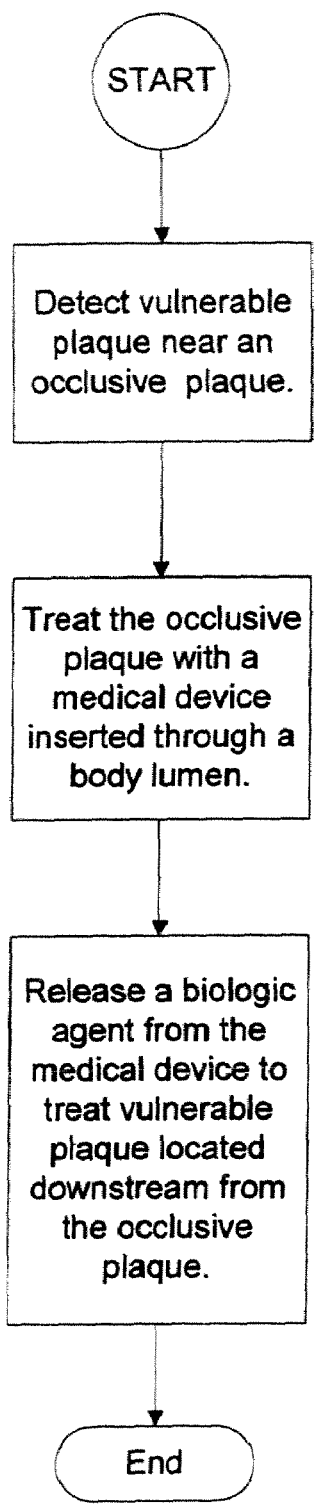
FIGS. 11A-11D illustrate various methods for treating vulnerable plaque.

FIG. 11A describes a method to treat vulnerable plaque downstream from an occlusive plaque. The occlusive plaque may be treated with a stent or balloon catheter. The vulnerable plaque may be treated by altering the lipid core and/or strengthening or thickening the fibrous cap surrounding the vulnerable plaque. The vulnerable plaque is first detected by any one of the techniques described above, including but not limited to IVUS, OCT, MRI, near infrared spectroscopy, thermography, and liquid crystal thermography. The vulnerable plaque may be downstream from an occlusive plaque that has been detected, for example, with an angiogram. A drug delivery catheter is provided having a vulnerable plaque stabilizing agent. In one embodiment, the drug delivery catheter may deploy a drug eluting stent. The drug eluting stent is positioned at the occlusive plaque to widen the arterial lumen whose blood flow has been impeded by the plaque. The vulnerable plaque stabilizing agent is released towards a vulnerable plaque region located downstream from the release site. Alternatively, the agents may be in the form of microparticles to control the release of the agents over time. The agents released from the drug delivery catheter may include lipid lowering agents, antioxidants, extracellular matrix synthesis promoters, or inhibitors of plaque inflammation and extracellular degradation.

Figure 11B:
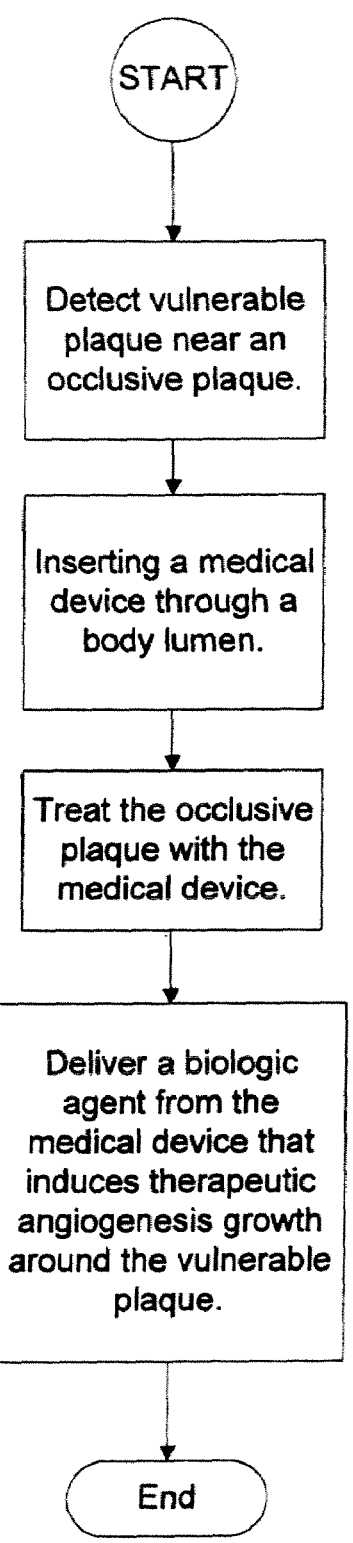

FIG. 11B describes a method to treat vulnerable plaque by inducing collateral artery or vessel growth to the myocardium downstream from or adjacent to an occlusive plaque. The occlusive plaque may be treated with a stent or balloon catheter. By inducing therapeutic angiogenesis (e.g., collateral artery or vessel growth), blood flow is maintained in case a vulnerable plaque ruptures leading to an occlusive thrombosis. The vulnerable plaque is first detected by any one of the techniques described above, including but not limited to IVUS, OCT, MRI, near infrared spectroscopy, thermography, and liquid crystal thermography. The vulnerable plaque may be downstream from an occlusive plaque that has been detected, for example, with an angiogram.

A drug delivery catheter or stent is provided having an agent that induces collateral artery or vessel growth. In one embodiment, the drug delivery catheter may deploy a drug eluting stent. The drug eluting stent is positioned at the occlusive plaque to widen the arterial lumen whose blood flow has been impeded by the plaque. The agent to induce collateral artery or vessel growth is released towards a vulnerable plaque region located downstream from the drug release site. Representative therapeutic or biologically active agents include, but are not limited to, proteins such as vascular endothelial growth factor (VEGF) in any of its multiple isoforms, fibroblast growth factors, monocyte chemoatractant protein 1 (MCP-1), transforming growth factor alpha (TGF-alpha), transforming growth factor beta (TGF-beta) in any of its multiple isoforms, DEL-1, insulin like growth factors (IGF), placental growth factor (PLGF), hepatocyte growth factor (HGF), prostaglandin E1 (PG-E1), prostaglandin E2 (PG-E2), tumor necrosis factor alpha (TBF-alpha), granulocyte stimulating growth factor (G-CSF), granulocyte macrophage colony-stimulating growth factor (GM-CSF), angiogenin, follistatin, and proliferin, genes encoding these proteins, cells transfected with these genes, pro-angiogenic peptides such as PR39 and PR11, and pro-angiogenic small molecules such as nicotine.

Figure 11C:
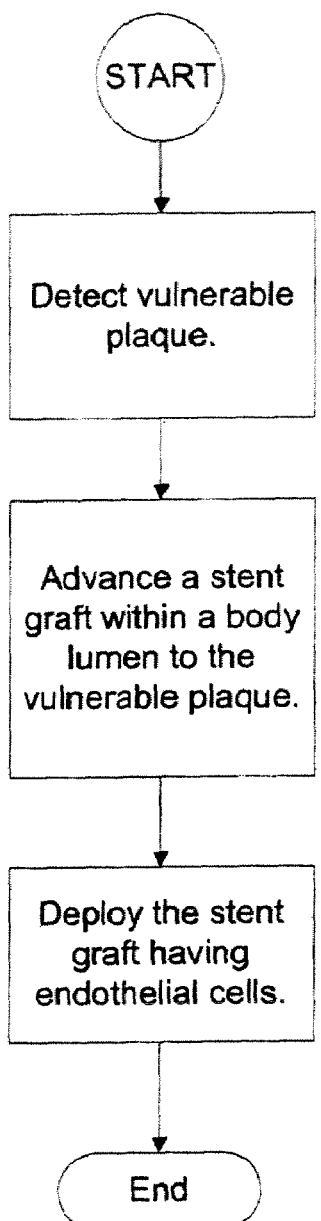

FIG. 11C describes a method to treat vulnerable plaque by implanting a stent graft on the arterial wall near a vulnerable plaque. This method of vulnerable plaque stabilization may be performed independent of treating an occlusive plaque. The vulnerable plaque is first detected by any one of the techniques described above, including but not limited to IVUS, OCT, MRI, near infrared spectroscopy, thermography, and liquid crystal thermography. The stent graft is disposed near a distal end of a catheter and advanced within the arterial lumen and positioned near a vulnerable plaque. Retracting a sheath covering the stent graft deploys the stent graft. In one embodiment, the stent graft has a thin ePTFE cylindrical tube affixed to the inner surface of a self-expandable stent. The inner surface of the stent has a layer of endothelial cells. The layer of endothelial cells promote cell migration that forms a fully lined monolayer on the arterial lumen surface. As such, the stent graft shields existing vulnerable plaque from an occlusive thrombotic event. Moreover, the stent graft provides reinforcement to the fibrous cap and reduces any physical stress placed on it due to the presence of the lipid core and hemodynamic forces.

Figure 11D:
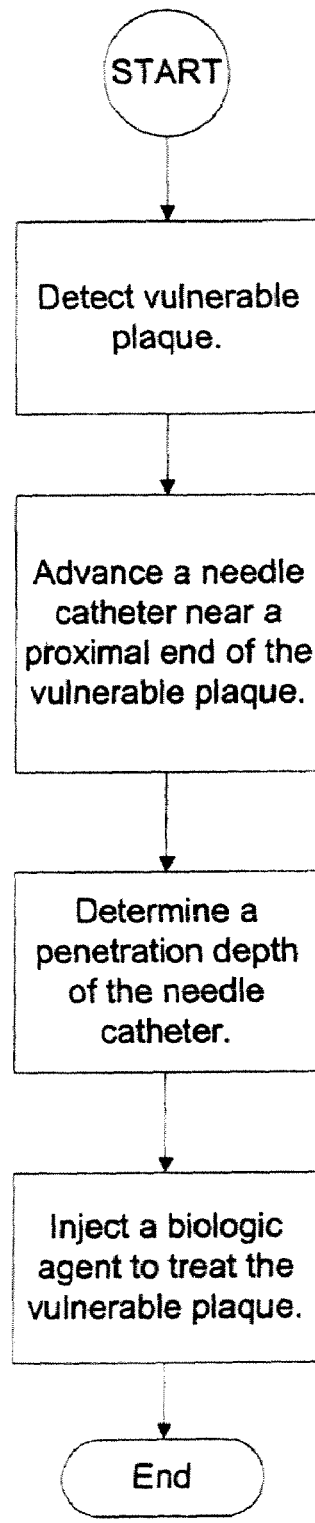

FIG. 11D describes another method to treat vulnerable plaque. The vulnerable plaque may be treated by injecting a stabilizing drug or biologically active agent at various locations within and around the vulnerable plaque. The vulnerable plaque is first detected by any one of the techniques described above, including but not limited to IVUS, OCT, MRI, near infrared spectroscopy, thermography, and liquid crystal thermography. A needle catheter is advanced through an arterial lumen and positioned near a proximal end of the vulnerable plaque. Alternatively, the needle catheter may be positioned at or near a distal end of the vulnerable plaque. A sensor disposed on the needle catheter determines a penetration depth for the needle catheter. The needle catheter may be adjusted to penetrate various targets around the vulnerable plaque including, but not limited to: fibrous cap, proteoglycan-rich surface layer, subintimal lipid core, proximal or distal regions of the vulnerable plaque, media containing smooth muscle cells above the lipid core and the adventitial space. The agents released from the drug delivery catheter may include lipid lowering agents, antioxidants, extracellular matrix synthesis promoters, inhibitors of plaque inflammation and extracellular degradation.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method comprising:
   implanting a stent graft into a body lumen near a vulnerable plaque region, wherein the stent graft has an expandable tube coupled to an inner surface of a stent and a layer of endothelial cells seeded on an inner surface of the expandable tube, and
   shielding the vulnerable plaque with the stent graft, wherein the stent graft prevents the vulnerable plaque from rupturing into the body lumen.

2. The method of claim 1, wherein implanting the stent graft comprises expanding the stent graft near the vulnerable plaque.

3. The method of claim 1, further comprising coating the stent graft with a vulnerable plaque biologically active agent.

4. The method of claim 3, further comprising treating the vulnerable plaque with the vulnerable plaque biologically active agent.

5. The method of claim 1, further comprising strengthening a fibrous cap of the vulnerable plaque.

6. The method of claim 1, wherein the stent graft comprises a material that is selected from the group consisting of a bioerodable material, a biodegradable polymeric material, a bioerodable material coated with a biologically active agent, and a biodegradable polymeric material coated with a biologically active agent.

7. The method of claim 1 further comprising forming a monolayer of the endothelial cells near the vulnerable plaque region.

8. The method of claim 7 wherein forming comprises the endothelial cells migrating from the inner surface of the expandable tube to a lumen wall near the vulnerable plaque.

* * * * *